United States Patent
Serhan et al.

(10) Patent No.: US 10,154,977 B2
(45) Date of Patent: Dec. 18, 2018

(54) ANTI-INFLAMMATORY PARTICLES

(75) Inventors: Charles N. Serhan, Needham, MA (US); Lucy V. Norling, Brookline, MA (US); Matthew Spite, Floyds Knobs, IN (US); Jesmond P. Dalli, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 140 days.

(21) Appl. No.: 14/006,118

(22) PCT Filed: Mar. 23, 2012

(86) PCT No.: PCT/US2012/030361
§ 371 (c)(1),
(2), (4) Date: Nov. 27, 2013

(87) PCT Pub. No.: WO2012/135032
PCT Pub. Date: Oct. 4, 2012

(65) Prior Publication Data
US 2014/0079631 A1 Mar. 20, 2014

Related U.S. Application Data

(60) Provisional application No. 61/467,704, filed on Mar. 25, 2011.

(51) Int. Cl.
| | |
|---|---|
| *A61K 31/202* | (2006.01) |
| *A61K 35/12* | (2015.01) |
| *A61K 35/14* | (2015.01) |
| *A61K 45/06* | (2006.01) |
| *A61K 49/00* | (2006.01) |
| *A61K 51/12* | (2006.01) |

(52) U.S. Cl.
CPC ............ *A61K 31/202* (2013.01); *A61K 35/12* (2013.01); *A61K 35/14* (2013.01); *A61K 45/06* (2013.01); *A61K 49/0052* (2013.01); *A61K 51/1244* (2013.01)

(58) Field of Classification Search
CPC ...... A61K 35/12; A61K 35/14; A61K 31/202; A61K 45/06; A61K 49/0052; A61K 51/1244
See application file for complete search history.

(56) References Cited

U.S. PATENT DOCUMENTS

| | | | | |
|---|---|---|---|---|
| 6,099,834 A | * | 8/2000 | Stanley | A01N 61/00 424/94.1 |
| 2002/0058259 A1 | * | 5/2002 | Ramakrishnan | C07K 14/705 435/6.16 |
| 2007/0243137 A1 | | 10/2007 | Hainfeld | |
| 2008/0069807 A1 | * | 3/2008 | Jy | A61K 35/18 424/93.72 |
| 2009/0156673 A1 | * | 6/2009 | Serhan | C07C 59/42 514/549 |

OTHER PUBLICATIONS

Mesri et al., The Journal of Biological Chemistry, 274(33):23111-23118 (1999). "Leukocyte microparticles stimulate endothelial cell cytokine release and tissue factor induction in a JNK1 signaling pathway."
Serhan et al., British Journal of Pharmacology, 153, issue S1:200-215 (2008). "Endogenous pro-resolving and anti-inflammatory lipid mediators: a new pharmacologic genus."
Vanwijk et al., Cardiovascular Research, 59:277-287 (2003). "Microparticles in cardiovascular diseases."
Wagner et al., Pharmacological Reviews, 52(3):349-374 (2000). "Neutrophil migration mechanisms, with an emphasis on the pulmonary vasculature."
Dalli, J. et al., Blood 112(6):2512-2519 (Sep. 15, 2008). "Annexin 1 mediates the rapid anti-inflammatory effects of neutrophil-derived microparticles."
Gasser, O. et al., Blood 104(8):2543-2548 (Oct. 15, 2004). Activated polymorphonuclear neutophils disseminate anti-inflammatory microparticles by ectocytosis.

* cited by examiner

*Primary Examiner* — Robert S Cabral
(74) *Attorney, Agent, or Firm* — Quarles & Brady LLP

(57) ABSTRACT

Described herein are compositions and methods relating to particles comprising at least one component of a cellular-derived microparticle. Aspects of technology described herein relate to compositions and methods for treating inflammation, wounds, and pain.

10 Claims, 14 Drawing Sheets

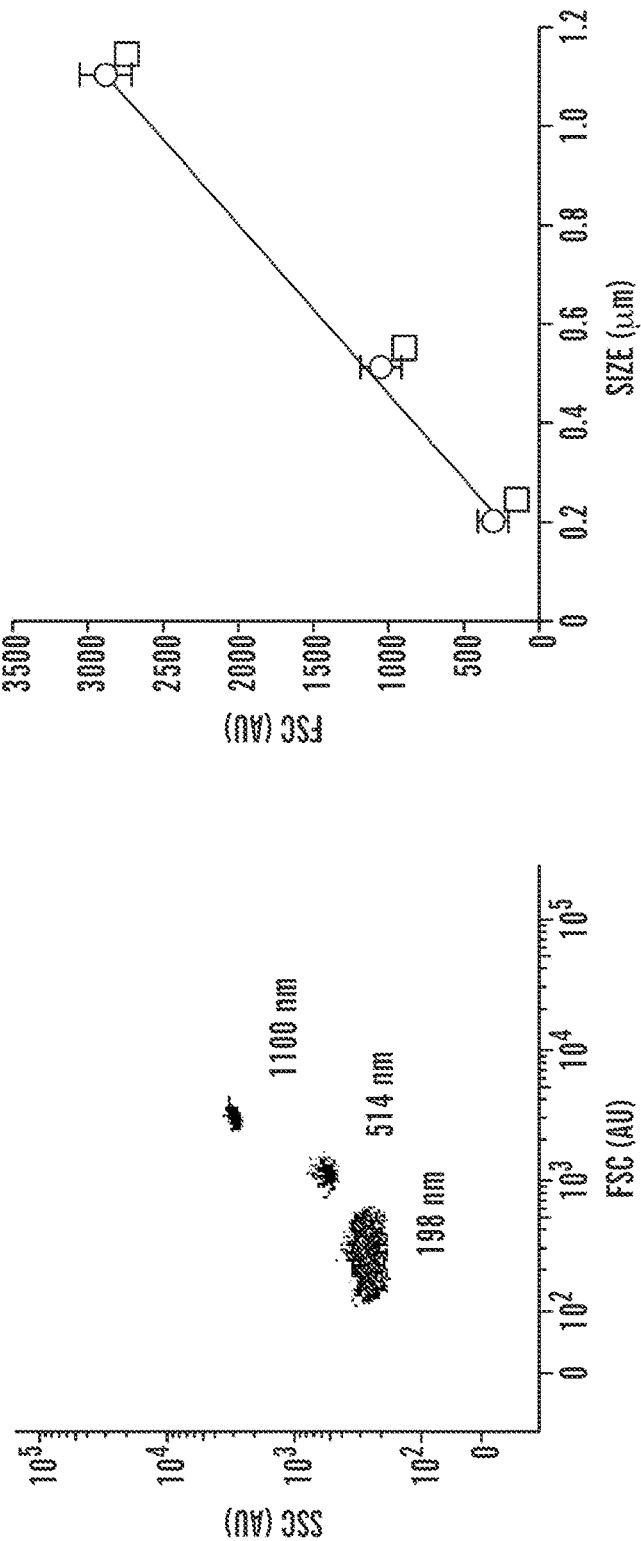

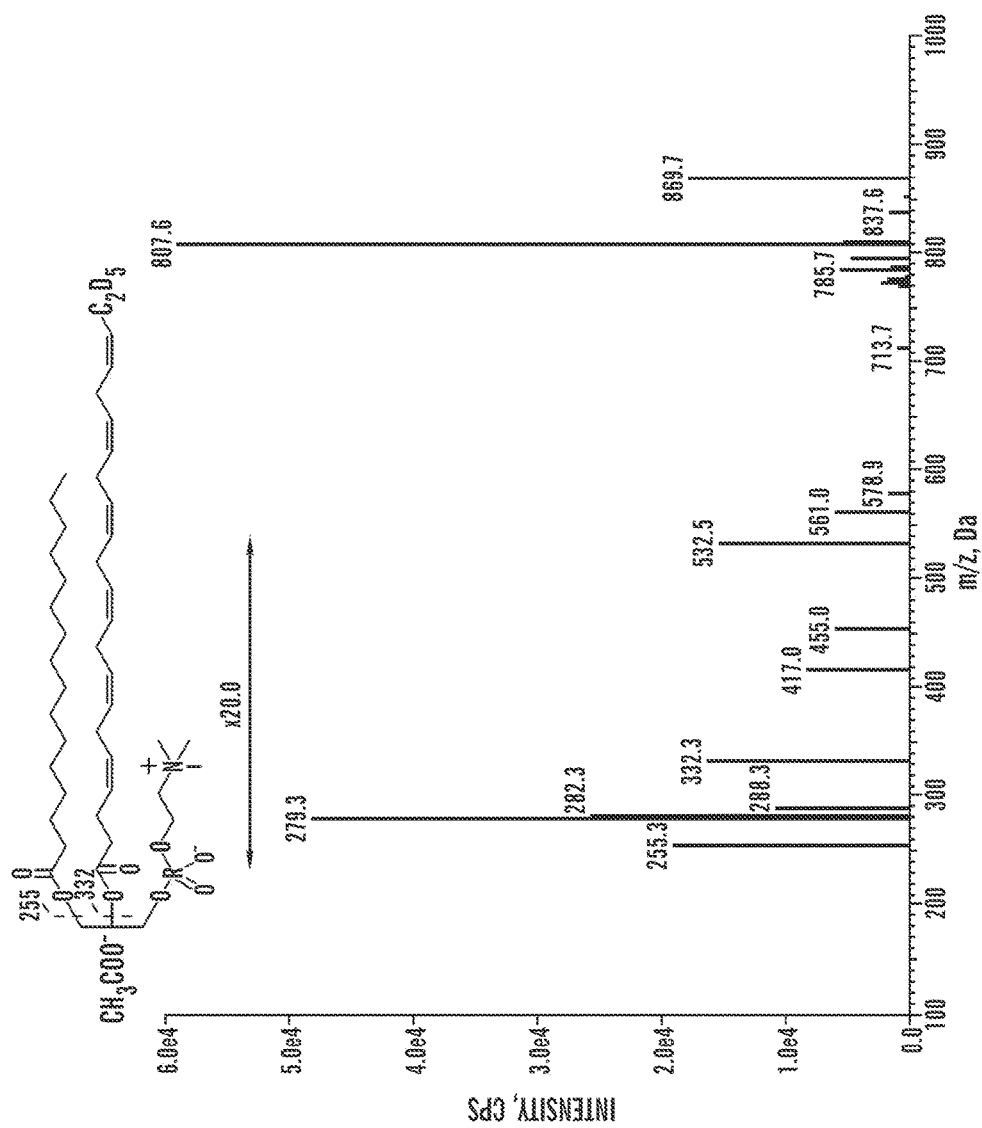

ANTI-INFLAMMATORY PARTICLES

CROSS REFERENCE TO RELATED APPLICATIONS

This application is a 35 U.S.C. § 371 National Phase Entry Application of International Application No. PCT/US2012/030361 filed Mar. 23, 2012, which designates the U.S., and which claims the benefit under 35 U.S.C. § 119(e) of U.S. Provisional Patent Application Ser. No. 61/467,704 filed Mar. 25, 2011, the contents of which are incorporated herein by reference in their entireties.

GOVERNMENT SUPPORT

The present application was made with Government support under Grant Numbers 1P01GM095467, 1R01DE019938, and 1P01GM38765 awarded by the National Institutes of Health. The Government of the United States has certain rights in the invention.

TECHNICAL FIELD

The disclosure relates to methods of treating inflammation and resolving wound healing by using particles.

BACKGROUND

Uncontrolled inflammation is a fundamental aetiology of many pathologies, including cardiovascular diseases, arthritis and temporomandibular joint disorders (TMDs) (Nathan, C., and A. Ding. 2010. *Cell* 140:871-882; Scrivani, S. J., et al. 2008. *N Engl J Med* 359:2693-2705). Prevalence of TMDs is high, with at least one symptom afflicting a third of US adults. However, treatment options for inflammatory conditions are limited and often involve behavioral or physical therapies or acute administration of nonsteroidal anti-inflammatories (Scrivani, S. J., et al. 2008. *N Engl J Med* 359:2693-2705). Timely resolution of an inflammatory insult is pertinent for restoration of tissue homeostasis and is essential for ongoing health (Gilroy, et al. 2004. *Nat Rev Drug Discov* 3:401416). Nanoparticle drug delivery systems have been explored for the treatment of numerous conditions, including inflammation, but the biomaterials used in these systems can activate the circulatory system and cause nanotoxicity, for example by uptake and activation of dendritic cells (Hess, H., and Y. Tseng. 2007 *ACS Nano* 1:390-392).

SUMMARY

The technology described herein is based upon the inventors' discovery that particles generated at least in part from cellular-derived microparticles have anti-inflammatory properties and can be used as drug delivery systems to treat, for example, inflammation, wounds, or pain.

In one aspect, the technology described herein relates to a particle comprising at least one component of a cellular-derived microparticle and at least one agent. In some embodiments, the cellular-derived microparticle is a microparticle generated during the initiation phase of an acute inflammatory response. In some embodiments, the cellular-derived microparticle is generated in vitro by cellular activation and has a pro-resolving microparticle phenotype. In some embodiments, the pro-resolving microparticle generated in vitro is a microparticle generated by contacting a cell with a leukocyte agonist. In some embodiments, the leukocyte agonist is selected from the group consisting of: IL-8; fMLP; IL-4; zymosan; LPS; leukotriene B4; and C5a. In some embodiments, the cellular-derived microparticle is a microparticle derived from leukocytes. In some embodiments, the cellular-derived microparticle is a microparticle derived from mammalian leukocytes. In some embodiments, the cellular-derived microparticle is a microparticle derived from human leukocytes.

In some embodiments, the at least one component of a cellular-derived microparticle is selected from the group consisting of: a hydroxy-docoshexaeonic acid (HDHA); 17-HDHA; 14-HDHA; 13-HDHA; 7-HDHA; 4-HDHA; a hydroxyl-eicostatentraenoic acid; a eicosanoid prostaglandin; a hydroxyl-eicosapentaenoic acid; and any combination thereof.

In some embodiments, the at least one component of a cellular-derived microparticle is selected from the group consisting of: Resolvin D1; Resolvin D2; Resolvin D3; Resolvin D5; Resolvin D6; Maresin 1; Protectin D1; Lipoxin $A_4$; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; and 5-HEPE.

In some embodiments, the agent is a therapeutic agent, an imaging agent, a micronutrient, a targeting agent, a tracking agent, or a chemotherapeutic agent. In some embodiments, the agent is selected from the group consisting of small organic or inorganic molecules; saccharines; oligosaccharides; polysaccharides; lipids, biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof.

In some embodiments, the agent is a lipid mediator. In some embodiments, the lipid mediator is selected from the group consisting of a Resolvin; Resolvin D1; Resolvin D2; Resolvin D3; Resolvin D5; Resolvin D6; aspirin-triggered Resolvin; aspirin-triggered Resolvin D1; aspirin-triggered Resolvin D2; aspirin-triggered Resolvin D3; Maresin 1; Protectin D1; 17-HDHA; 14-HDHA; 13-HDHA; 7-HDHA; 4-HDHA; a Lipoxin; a Lipoxin analog; Lipoxin $A_4$; a Lipoxin $A_4$ analog; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; 5-HEPE; Annexin A1; and analogs or mimetics thereof.

In some embodiments, the agent is a therapeutic agent selected from the group consisting of anti-inflammatory agents, anti-infective agents, antibiotics, pro-resolving drugs; and antinociceptives. In some embodiments, the therapeutic agent is selected from the group consisting of: nonsteroidal anti-inflammatory drugs; glucocorticoids, CO-donor compounds, and NO-donor compounds.

In some embodiments, the agent is an imaging agent selected from the group consisting of a fluorescent dye; a fluorescent imaging agent; a radioisotope; and a MRI contrast agent.

In some embodiments, the agent is a targeting agent selected from the group consisting of peptides, polypeptides, proteins, peptidomimetics, glycoproteins, lectins, nucleosides, nucleotides, nucleic acids, monosaccharides, disaccharides, trisaccharides, oligosaccharides, polysaccharides, lipopolysaccharides, vitamins, steroids, hormones, cofactors, receptors, receptor ligands, antibodies, antigen binding fragments of antibodies, and analogs and derivatives thereof. In some embodiments, the particle comprises both a targeting agent and at least one of a therapeutic agent, an imaging agent, a micronutrient, a tracking agent, or a chemotherapeutic agent.

In some embodiments, the agent comprises about 0.01 wt % to about 99 wt % of the particle. In some embodiments, $10^5$ particles comprise from about 0.01 ng to about 100 ng of the agent. In some embodiments, $10^5$ particles comprise from about 5 ng to about 15 ng of the agent.

In some embodiments, the particle is of a size from about 100 nm to about 1.5 μm in diameter. In some embodiments, the particle is of a diameter selected from the group consisting of: about 200 nm; about 500 nm; and about 1100 nm.

In one aspect, the technology described herein relates to a method of preparing a particle comprising; providing a cellular-derived microparticle; and sonicating the microparticle in the presence of at least one agent. In some embodiments, the sonication occurs at 1 to 100 W. In some embodiments, the sonication occurs at about 15 W.

In some embodiments, the cellular-derived microparticle is a microparticle derived from leukocytes. In some embodiments, the cellular-derived microparticle is a microparticle derived from mammalian leukocytes. In some embodiments, the cellular-derived microparticle is a microparticle derived from human leukocytes. In some embodiments, the cellular-derived microparticles are obtained from a subject's blood sample.

In some embodiments, the method further comprises contacting leukocytes in a sample obtained from a subject with a leukocyte agonist. In some embodiments, the cellular-derived microparticle is a microparticle generated during the initiation phase of an acute inflammatory response. In some embodiments the cellular-derived microparticle is generated in vitro by cellular activation and has a pro-resolving microparticle phenotype. In some embodiments, the pro-resolving microparticle generated in vitro is a microparticle generated by contacting a cell with a leukocyte agonist. In some embodiments, the leukocyte agonist is selected from the group consisting of: IL-8; fMLP; IL-4; zymosan; LPS; leukotriene B4; and C5a.

In some embodiments, the method further comprises a step selected from the group consisting of filtration, centrifugation, or combination thereof, thereby selecting particles of desire size. In some embodiments, the method further comprises selecting the particle of size from about 100 nm to about 1.5 μm. In some embodiments, the method further comprises selecting the particle of size from about 200 nm, about 500 nm, or about 1100 nm.

In some embodiments, the particle comprises at least one component of a cellular-derived microparticle selected from the group consisting of: a hydroxy-docoshexaeonic acid (HDHA); 17-HDHA; 14-HDHA; 13-HDHA; 7-HDHA; 4-HDHA; a hydroxyl-eicostatentraenoic acid; a eicosanoid prostaglandin; a hydroxyl-eicosapentaenoic acid; and any combination thereof. In some embodiments, the particle comprises at least one component of a cellular-derived microparticle selected from the group consisting of: Resolvin D1; Resolvin D2; Resolvin D3; Resolvin D5; Resolvin D6; Maresin 1; Protectin D1; Lipoxin $A_4$; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; and 5-HEPE.

In some embodiments, the agent is selected from the group consisting of: a therapeutic agent, an imaging agent, a micronutrient, a targeting agent, a tracking agent, a chemotherapeutic agent. In some embodiments, the agent is selected from the group consisting of small organic or inorganic molecules; saccharines; oligosaccharides; polysaccharides; lipids, biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof.

In some embodiments, the agent is a lipid mediator. In some embodiments, the lipid mediator is selected from the group consisting of: a Resolvin; Resolvin D1; Resolvin D2; Resolvin D3; Resolvin D5; Resolvin D6; aspirin-triggered Resolvin; aspirin-triggered Resolvin D1; aspirin-triggered Resolvin D2; aspirin-triggered Resolvin D3; Maresin 1; Protectin D1; 17-HDHA; 14-HDHA; 13-HDHA; 7-HDHA; 4-HDHA; a Lipoxin; a Lipoxin analog; Lipoxin $A_4$; a Lipoxin $A_4$ analog; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; 5-HEPE; Annexin A1; and analogs or mimetics thereof.

In some embodiments, the therapeutic agent is selected from the group consisting of anti-inflammatory agents, anti-infective agents, antibiotics, pro-resolving drugs; and antinociceptives. In some embodiments, the therapeutic agent is selected from the group consisting of nonsteroidal anti-inflammatory drugs; glucocorticoids, CO-donor compounds, and NO-donor compounds.

In some embodiments, the agent is an imaging agent selected from the group consisting of a fluorescent dye; a fluorescent imaging agent; a radioisotope; and a MRI contrast agent.

In some embodiments, the agent is a targeting agent selected from the group consisting of peptides, polypeptides, proteins, peptidomimetics, glycoproteins, lectins, nucleosides, nucleotides, nucleic acids, monosaccharides, disaccharides, trisaccharides, oligosaccharides, polysaccharides, lipopolysaccharides, vitamins, steroids, hormones, cofactors, receptors, receptor ligands, antibodies, antigen binding fragments of antibodies, and analogs and derivatives thereof. In some embodiments, the particle comprises both a targeting agent and at least one of a therapeutic agent, an imaging agent, a micronutrient, a tracking agent, or a chemotherapeutic agent.

In some embodiments, the agent comprises about 0.01 wt % to about 99 wt % of the particle. In some embodiments, $10^5$ particles comprise from about 0.01 ng to about 100 ng of the agent. In some embodiments, $10^5$ particles comprise from about 5 ng to about 15 ng of the agent.

In some embodiments, the method further comprises determining the effectiveness of a particle by performing a tissue regeneration assay. In some embodiments, the tissue regeneration assay is a Platyhelminthes tissue regeneration assay.

In one aspect, the technology described herein relates to a particle prepared by the methods described herein.

In one aspect, the technology described herein relates to a pharmaceutical composition comprising a particle as described herein and a pharmaceutically acceptable carrier.

In one aspect, the technology described herein relates to a method comprising: administering a particle or composition described herein to a subject. In some embodiments, the subject is in need of treatment for inflammation, wound healing, or pain management. In some embodiments, the inflammation is selected from the group consisting of: skin inflammation; inflammation caused by substance abuse or drug addiction; inflammation associated with infection; inflammation of the cornea; inflammation of the retina; inflammation of the spinal cord; inflammation associated with organ regeneration; and pulmonary inflammation. In some embodiments, the subject is in need of treatment for a condition selected from the group consisting of: temporomandibular joint disorders; COPD; smoke-induced lung injury; renal dialysis associated disorders; spinal cord injury; graft vs. host disease; bone marrow transplant or complications thereof; infection; trauma; pain; incisions; surgical incisions; a chronic pain disorder; a chronic bone disorder; mastitis; and joint disease.

In some embodiments, said administration is injection, infusion, instillation, inhalation, ingestion, or topical. In some embodiments, the administration is local or systemic. In some embodiments, the particle is autologous to the subject. In some embodiments, the particle comprises a therapeutically effective amount of the agent.

The details of various embodiments are set forth in the description below. Other features, objects, and advantages will be apparent from the description and the drawings, and from the claims.

DESCRIPTION OF THE DRAWINGS

FIG. 1A depicts a time course of PMN and mononuclear cell accumulation, and MP generation following zymosan-induced murine peritonitis (1 mg i.p). Inset: Representative 4 h MP flow cytometry plot. FIG. 1B depicts characterization of endogenous MPs from exudates at indicated time points. Results are mean±SEM (n=3-7 per time point).

FIG. 2A depicts MPs collected from zymosan (1 mg i.p.) exudates and extracted for targeted lipidomics. LM biosynthetic pathway markers 17-HDHA (diamond markers) and 14-HDHA (square markers) identified using scheduled MRM. FIG. 2B depicts representative mass spectrum of 17-HDHA within endogenous MPs. FIG. 2C depicts the results obtained when mice were administered $d_5$-DHA (1 μg i.v.) followed by zymosan (1 mg i.p.) and MPs collected from 4 h lavages. Both $d_5$-17-HDHA and $d_5$-14-HDHA were identified (transition pairs 348.2/245.1 and 348.2/205.1). Representative of n=3 per time point.

FIGS. 3A-3G depict the construction and characterization of humanized nano pro-resolving medicines (NPRMs). FIG. 3A demonstrates the sizes of particles. Human PMN-derived MPs isolated and enriched with AT-RvD1 or o[9,12]-benzo-w6-epi-LXA$_4$ and fluorescent 1,2-dioleoyl-glycero-3-phospho-L-serine-N (7-nitro-2-1,3-benzoxadiazo-4-yl). Enriched NPRMs were separated by size-exclusion chromatography and sized by flow cytometry. Both populations are shown. In FIG. 3B fluorescence incorporation into NPRM (right peak) was monitored by flow cytometry. In FIGS. 3C-3D, NPRM sizing was determined using cytometry calibration beads. In FIGS. 3E and 3F, sizing was also validated using electron microscopy of MPs and NPRMs following negative staining; calibration nanospheres are shown inset. In FIG. 3G, incorporation of AT-RvD1 into NPs was determined using LC-MS/MS with representative mass spectra.

FIG. 4A depicts the results of peritoneal PMN infiltration 2 h after administration of zymosan (100 μg i.p.). Mice were treated with vehicle, NPs ($1\times10^5$), LXA$_4$ analog (300 ng), or LXA$_4$ analog NPRMs ($1\times10^5$). In FIG. 4B, mice were given vehicle or AT-RvD1 NPRMs ($1\times10^5$ i.v.) before zymosan (100 μg i.p.), and the resolution interval ($R_i$) of acute inflammation was calculated. In FIG. 4C, wound healing of keratinocytes was assessed in vitro following treatment with vehicle, NPs, AT-RvD1 (10 nM) or AT-RvD1 (10 nM) NPRMs (n=3). FIG. 4D demonstrates that PRMs limit PMN infiltration to CFA-inflamed TMJs. Mice administered CFA (10 μg, 20 μl, periarticular) to the left TMJ and saline (20 μl) into the right TMJ followed by i.v. treatment with buffer (10 μl PBS), ATRvD1 (10 ng) NPRMs or LXA$_4$ analog (10 ng) NPRMs, and 12 h MPO tissue levels were assessed in CFA-inflamed TMJ (n=3-7 per treatment group). Values are mean±SEM. *p<0.05, **p<0.01.

FIGS. 5A-5B demonstrate that exogenous d5-DHA is incorporated into MP phospholipids. Human PMN ($25\times10^6$) were incubated with $d_5$-DHA (5 μg) for 30 min, 37° C. and MPs were collected to assess whether exogenous DHA could be detected within MP phospholipids. Tandem mass spectra of biogenic (FIG. 5A) hexadecanoyl-docosahexaenoyl phosphatidylcholine and (FIG. 5B) hexadecanoyl-hydroxydocosahexaenoyl phosphatidylcholine. Acyl group positions are arbitrarily assigned. Compounds were identified as acetate adducts in negative ionization mode using Qstar-XL.

(FIG. 7B) i.p. as indicated prior to zymosan A (0.1 mg, i.p) and peritoneal PMN infiltration was assessed at 2 h.

DETAILED DESCRIPTION OF EXEMPLARY EMBODIMENTS

Figure 1A:
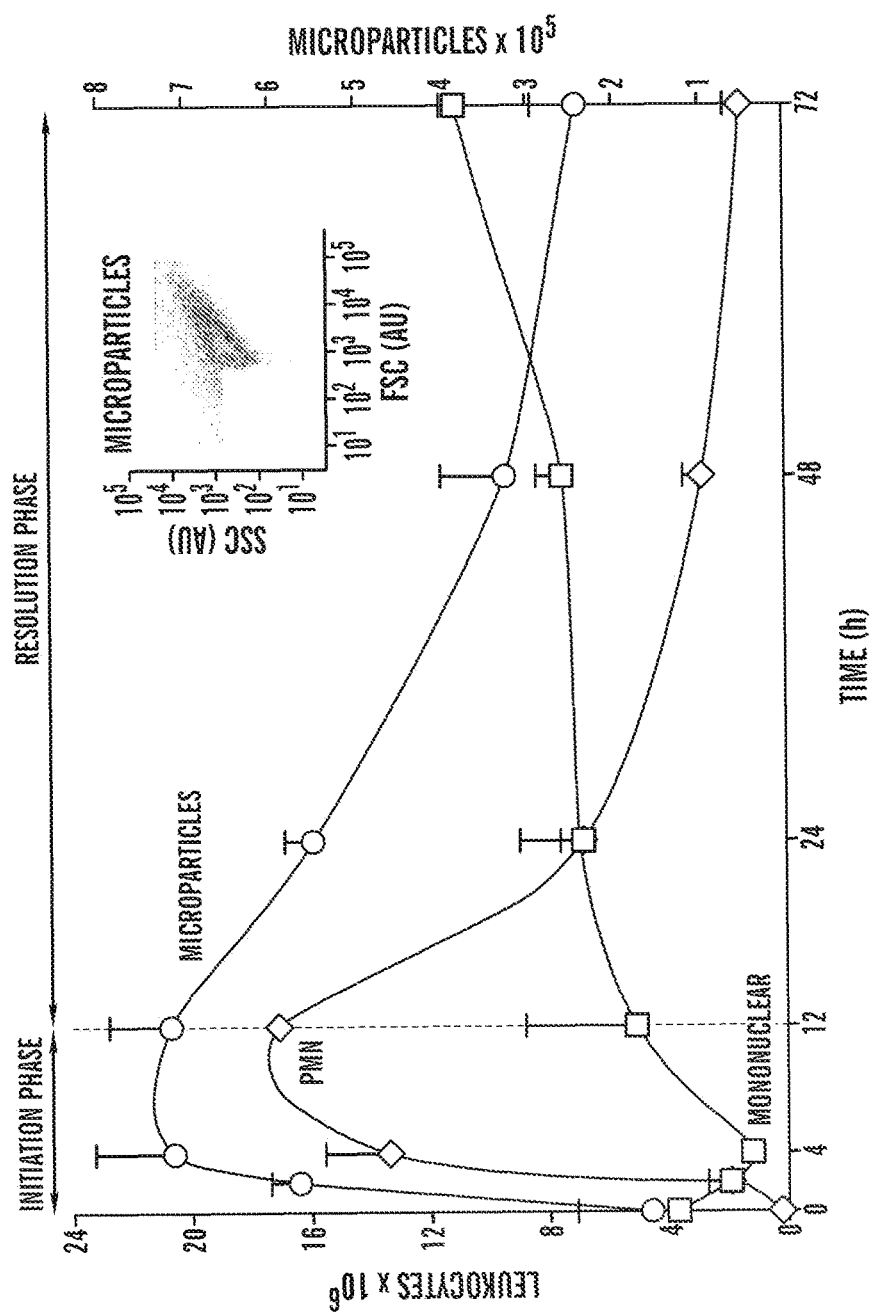
FIGS. 1A-1B depict the temporal production of endogenous leukocyte-derived microparticles during peritonitis.

Described herein are compositions and methods based upon the inventors' discovery that material obtained from anti-inflammatory cellular-derived microparticles can be used to generate particles useful in treating inflammatory conditions. The anti-inflammatory properties of these particles can be augmented by incorporating additional pharmaceutically active agents into the particles. In some embodiments, the additional pharmaceutically active agents are lipid mediators. In some aspects of the technology described herein, the particles described here can be drug delivery systems for use in treating conditions not necessarily related to inflammation (e.g. cancer).

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.) and The Encyclopedia of Molecular Biology, published by Blackwell Science Ltd., 1994 (ISBN 0-632-02182-9); Definitions of common terms in molecular biology can also be found in Benjamin Lewin, Genes X, published by Jones & Bartlett Publishing, 2009 (ISBN-10: 0763766321); and Kendrew et al. (eds.), Molecular Biology and Biotechnology: a Comprehensive Desk Reference, published by VCH Publishers, Inc., 1995 (ISBN 1-56081-569-8). Unless otherwise stated, the present invention was performed using standard procedures, as described, for example in Davis et al., Basic Methods in Molecular Biology, Elsevier Science Publishing, Inc., New York, USA (1995) and Current Protocols in Cell Biology (CPCB) (Juan S. Bonifacino et. al. ed., John Wiley and Sons, Inc.), which are all incorporated by reference herein in their entireties.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to a reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of inflammation, delay or slowing of inflammation, and amelioration or palliation of inflammation.

As used herein, the phrase "therapeutically effective amount", "effective amount" or "effective dose" refers to an amount that provides a therapeutic or aesthetic benefit in the treatment, prevention, or management of, for example, inflammation or wound healing, e.g. an amount that provides a statistically significant decrease in at least one symptom, sign, or marker of inflammation and/or wound healing. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutical composition" refers to the active agent in combination with a pharmaceutically acceptable carrier commonly used in the pharmaceutical industry.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, inflammation. In addition, the methods described herein can be used to treat domesticated animals and/or pets. A subject can be male or female.

A subject can be one who has been previously diagnosed with or identified as suffering from or having a condition in need of treatment (e.g. inflammation) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors.

As used herein, the term "administering," refers to the placement of a particle as described herein into a subject by a method or route which results in at least partial localization of the agents at a desired site. The pharmaceutical compositions of comprising a particle as described herein can be administered by any appropriate route which results in an effective treatment in the subject, including, but not limited to, orally, by injection, transdermally, by direct application (e.g. to the skin or eye or to tissue exposed by, for example, surgery or injury), subcutaneous, intravenous (including bolus injection), intramuscular, intrathecal, and intraarterial.

As used herein the term "comprising" or "comprises" is used in reference to compositions, methods, and respective component(s) thereof, that are useful to the method or composition, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word or is intended to include and unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

Described herein are particles derived from cellular-derived microparticles and methods of producing and using such particles. As used herein, a "particle" refers to a vesicle comprising a lipid bi-layer and an interior, aqueous space surrounded by the lipid bilayer. A particle can comprise at least one component of a cellular-derived microparticle and at least one agent. The terms "particle" and "nano pro-resolving medicines" are used interchangeably herein.

As used herein, "a cellular-derived microparticle" refers to a vesicle formed from a fragment of the plasma membrane of a eukaryotic cell and shed by the cell. Cellular-derived microparticles can be 2500 nm or less in diameter, e.g. 1500 nm, 1200 nm, 1000 nm, 800 nm or less in diameter. The interior space of a cellular-derived microparticle can comprise proteins, nucleic acids, or other biological materials. A cellular-derived microparticle can be formed and shed in response to a stimuli or it can be formed and shed spontaneously. A cell producing a cellular-derived microparticle can be a mammalian cell, e.g. human, primate, mouse, rat, or pig cell. A cell producing a cellular-derived microparticle can be a transgenic cell or a cell obtained from a transgenic and/or chimeric organism, e.g. the cell can be a human cell produced by a mouse having human or humanized leukocytes. Cellular-derived microparticles generated by non-human cells can be useful in, for example, veterinary applications, e.g. to treat cows, horses, pets, or domesticated animals according to the methods described below herein. Non-limiting examples include treating mastitis in cows or arthritis in equines.

In some embodiments, the cellular-derived microparticle can be a leukocyte-derived microparticle. As used herein, "leukocyte-derive microparticle" refers to a cellular-derived microparticle which originates from a leukocyte. Leukocyte-derived microparticles can be derived from any type of leukocyte, e.g. neutrophils, basophils, eosinophils, lymphocytes, monocytes, or macrophages. In some embodiments, the leukocytes are mammalian leukocytes. In some embodiments, the leukocytes are human leukocytes. In some embodiments, the leukocyte-derived microparticles can be derived from granulocytes or polymorphonuclear leukocytes, e.g. neutrophils, basophils, or eosinophils. In some embodiments, the polymorphonuclear leukocytes are mammalian polymorphonuclear leukocytes. In some embodiments, the polymorphonuclear leukocytes are human polymorphonuclear leukocytes. In some embodiments, the leukocyte-derived microparticles can be derived from neutrophils. In some embodiments, the neutrophils are mammalian neutrophils. In some embodiments, the neutrophils are human neutrophils. By way of non-limiting example, cellular-derived microparticles originating from polymorphonuclear leukocytes can be distinguished from microparticles originated from other cell types (e.g. lymphocytes, platelets, and endothelial cells) by the expression of, for example, CD62L and CD11b on the surface of the microparticle.

Cellular-derived microparticles generated during a cellular response can have enhanced levels of a given biological activity, can be more abundant, or can be more homogeneous. In some embodiments, the cellular-derived microparticles used in the compositions and methods described herein can be cellular-derived microparticles generated during the initiation phase of an acute inflammatory response. An acute inflammatory response is characterized by increased movement of plasma and leukocytes from the blood into the affected tissues. Acute inflammatory responses are typically short-term processes, often beginning within minutes or hours of the inflammatory stimulus and ending upon removal of the stimulus. Acute inflammation can be characterized by one or more of redness, increased heat, swelling, pain, and loss of function. Molecular markers of an acute inflammatory response can include one of more of the release of vasoactive amines, eicosanoids, and bradykinin; as well as activation of the complement, coagulation, and fibrinolysis systems. Acute inflammation responses can be contrasted with a chronic inflammation response which is prolonged and delayed. Chronic inflammation involves a progressive shift in the type of cells that are present at the site of inflammation, and often leads to simultaneous or near simultaneous destruction and healing of the tissue from the inflammatory process. At the cellular level, chronic inflammatory responses involve a variety of immune cells such as monocytes, macrophages, lymphocytes, plasma cells, and fibroblasts, though in contrast to acute inflammation, which is mediated mainly by granulocytes, chronic inflammation is mainly mediated by mononuclear cells such as monocytes and lymphocytes. Chronic inflammation also involves a variety of inflammatory mediators, such as IFN-γ and other cytokines, growth factors, reactive oxygen species, and hydrolytic enzymes. Chronic inflammation can last for many months or years, and can result in undesired tissue destruction and fibrosis. The initiation phase of an acute inflammation response is the portion of the acute inflammatory response characterized by rapid infiltration of, for example, polymorphonuclear neutrophils (PMNs) followed by the infiltration of monocytes that mature into macrophages, and edema formation in response to inflammatory stimuli. The initiation phase is distinct from the later resolution phase in which PMNs undergo apoptosis and are ingested by macrophages that emigrate rapidly from the inflamed site to the draining lymph nodes. An acute inflammatory response can be naturally occurring or can be induced by contacting a cell or an organism with an agent that causes an acute inflammatory response.

In some embodiments, the cellular-derived microparticle can be generated in vitro by cellular activation. Cellular activation can include causing a cell or population of cells to be contacted with a stimulus that causes the generation of microparticles, an increase in the generation of microparticles, or the generation of microparticles with a particular phenotype. In some embodiments, the cellular-derived microparticle can have a pro-resolving microparticle phenotype. As used herein the term "pro-resolving microparticle phenotype" refers to a microparticle that, in its endogenous form, promotes the resolution of an inflammatory response, e.g. it decreases at least one sign or symptom of inflammation. In some embodiments, cellular activation can comprise contacting a leukocyte with a leukocyte agonist, which is described below herein.

In some embodiments, the cellular-derived microparticles for use in the compositions and methods described herein are generated by contacting leukocytes with a leukocyte agonist. As used herein, a "leukocyte agonist" is any agent which is capable of initiating an acute inflammatory response from at least a leukocyte (i.e. it can activate a leukocyte) at the dose used. Non-limiting examples of leukocyte agonists include fMLP (formyl-methionyl-leucyl-phenylalanine); zymosan, LPS, IL-4, Il-8, leukotriene B4, and complement factor C5a. Leukocyte agonists are available commercially, for example, zymosan A (Cat No:Z4250 Sigma-Aldrich; St. Louis, Mo.). In some embodiments, the leukocyte agonist is fMLP. In some embodiments, the leukocyte agonist is IL-8.

Methods of generating and isolating microparticles are known in the art and are described, for example in Gasser and Schifferli Blood 2004 104:2543-2548 and Dalli et al Blood 2008 112:2512-9; which are incorporated by reference herein in their entirety. By way of non-limiting example, PMNs can be prepared by gradient separation and added to endothelial monolayers in culture. PMNs can be contacted with a leukocyte agonist, e.g. 1 μM fMLP for 1 hour, and microparticles can be collected by centrifuging the supernatant, e.g. 4000 g for 5 min followed by 100,000 g for 1 hour. Microparticles can be resuspended in PBS. In some embodiments, the microparticles can be generated by cultured cells. In some embodiments, the microparticles can be generated by primary cells. In some embodiments, the microparticles can be generated by cells in a blood sample. In some embodiments, the microparticles can be generated by cells isolated from a blood sample. In some embodiments, the microparticles can be generated by cells comprised by a sample obtained from a subject.

The particles described herein can comprise at least one component of a cellular-derived microparticle. A component of a cellular-derived microparticle can be any material which is endogenous to the cellular-derived microparticle. By way of non-limiting example, a component of a cellular-derived microparticle can be a phospholipid, a signaling molecule, fatty acids, plasma membrane protein, receptor, ligand, CD11b, CD62L (cell surface L-selectin), RNA molecules, cytoplasmic proteins, endogenous anti-inflammatory compounds, interleukins, phosphatidylserine, annexin 1, myeloperoxidase, elastase, and proteolytic enzymes. In some embodiments, a particle as described herein can comprise at least 1 component of a cellular-derived microparticle, e.g. 1 component, 2 components, 3 components, 4 components, 5 components, or more components of a cellular-derived microparticle.

In some embodiments, the at least one component of a cellular-derived microparticle is selected from the group consisting of a hydroxy-docoshexaeonic acid (HDHA); 17-HDHA; 14-HDHA; 13-HDHA; 7-HDHA; 4-HDHA; a hydroxyl-eicostatentraenoic acid; a eicosanoid prostaglandin; a hydroxyl-eicosapentaenoic acid; and any combination thereof. In some embodiments, the at least one component of a cellular-derived microparticles is a hydroxy-docosahexaenoic acid (HDHA). HDHA and analogs thereof are well known in the art (see, for example U.S. Pat. Nos. 7,585,856; 7,759,395 and U.S. Patent Publications 2009/01566732011/0288317; which are incorporated by reference herein in their entireties). In some embodiments, the HDHA can be 14-HDHA or 17-HDHA. Further non-limiting examples of HDHA's include 7-HDHA, 4-HDHA, 10-HDHA, and 13-HDHA. HDHA's can comprise one or more hydroxy groups, e.g. 1 hydroxy group, 2 hydroxy groups, 3 hydroxy groups or more hydroxy groups.

In some embodiments, the at least one component of a cellular-derived microparticle is selected from the group consisting of Resolvin D1; Resolvin D2; Resolvin D3; Resolvin D5; Resolvin D6; Maresin 1; Protectin D1; Lipoxin $A_4$; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; and 5-HEPE.

The particles described herein can comprise at least one agent, e.g. a particle can comprise 1 agent, 2 agents, 3 agents, 4 agents, or more agents. As used herein, an "agent" refers to any molecule or combination of molecules added to a particle during construction which is either a) not present in the cellular-derived microparticle used to construct the particle, or b) is present in the cellular-derived microparticle at a lower concentration than in the resulting particle. An agent can be, by way of non-limiting example, a therapeutic agent, an imaging agent, a micronutrient, a targeting agent, a tracking agent, a lipid mediator, or a chemotherapeutic agent. An agent can be a small organic or inorganic molecule; a saccharine; an oligosaccharides; a polysaccharide; a lipid, a biological macromolecule, e.g., a peptide, a protein, and peptide analogs and derivatives; a peptidomimetic; a nucleic acid; a nucleic acid analog or derivative; an antibody or antigen binding fragment thereof; an extract made from biological materials such as bacteria, plants, fungi, or animal cells; an animal tissue; a naturally occurring or synthetic composition; or any combination thereof.

The particles described herein can be used to deliver agents of therapeutic value to a subject, particularly to sites of inflammatory activity. In some embodiments, a particle can comprise an agent which is a therapeutic agent. As used herein, the term "therapeutic agent" refers to a biological or chemical agent used for treatment, curing, mitigating, or preventing deleterious conditions in a subject. The term "therapeutic agent" also includes substances and agents for combating a disease, condition, or disorder of a subject, and includes drugs, diagnostics, and instrumentation. "Therapeutic agent" also includes anything used in medical diagnosis, or in restoring, correcting, or modifying physiological functions. The terms "therapeutic agent" and "pharmaceutically active agent" are used interchangeably herein.

The therapeutic agent can be selected according to the treatment objective and biological action desired. General classes of therapeutic agents include anti-microbial agents such as adrenergic agents, antibiotic agents or antibacterial agents, antiviral agents, anthelmintic agents, anti-inflammatory agents, antineoplastic agents, antioxidant agents, biological reaction inhibitors, botulinum toxin agents, chemotherapy agents, diagnostic agents, gene therapy agents, hormonal agents, mucolytic agents, radioprotective agents, radioactive agents including brachytherapy materials, tissue growth inhibitors, tissue growth enhancers, and vasoactive agents. The therapeutic agent can be selected from any class suitable for the therapeutic objective. For example, if the objective is treating a disease or condition associated with inflammation, the therapeutic agent can include anti-inflammatory agents, e.g. lipid mediators. By way of further example, if the desired treatment objective is treatment of cancer, the therapeutic agent can include radioactive material in the form of radioactive molecules providing radiation treatment directly into the tumor or close to it. Further, the therapeutic agent can be selected or arranged to provide therapeutic activity over a period of time. Exemplary pharmaceutically active compound include, but are not limited to, those found in Harrison's Principles of Internal Medicine, 13th Edition, Eds. T. R. Harrison et al. McGraw-Hill N.Y., NY; Physicians' Desk Reference, 50th Edition, 1997, Oradell, N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the complete content of all of which are herein incorporated in its entirety. In some embodiments, a therapeutic agent can be a chemotherapeutic agent. In some embodiments, a therapeutic agent can be an anti-inflammatory agent. In some embodiments, a therapeutic agent can be an anti-infective agent or antibiotic.

In some embodiments, the agent can be an anti-inflammatory agent. Anti-inflammatory agents can include the lipid mediators described herein below as well as anti-inflammatory agents which are not lipid mediators. Exemplary anti-inflammatory agents include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); anti-malarial medication (such as hydrochloroquine); methotrexate; sulfasalazine; leflunomide; anti-TNF medications; cyclophosphamide; pro-resolving drugs; mycophenolate; NO-donors (e.g. S-nitrosothiols, oximes, diazeniumdiolates, syndnonimines, and N-hydroxyguandines, glyceryl trinitrate, isosorbide mononitrate, pentaerythrityl tetranitrate, sodium nitroprusside, NCX4215, NCX4016, nicorandil, pravastatin, nipradilol, and nitro-pravastatin) and CO-donors (e.g. hemin, CORM-2, $[MN_2(CO)_{10}]$, and $[Ru(CO)_3Cl_2]_2$).

In some embodiments, an agent can be a lipid mediator. As used herein, the term "lipid mediator" refers to a lipid-derived compound that promotes the resolution of inflammation, e.g. it can reduce one sign or symptom of inflammation in a cell or organism. Examples of lipid mediators include, but are not limited to a Resolvin; Resolvin D1; Resolvin D2; Resolvin D3; Resolvin D5; Resolvin D6; aspirin-triggered Resolvin; aspirin-triggered Resolvin D1; aspirin-triggered Resolvin D2; aspirin-triggered Resolvin D3; Maresin 1; Protectin D1; 17-HDHA; 14-HDHA; 13-HDHA; 7-HDHA; 4-HDHA; a Lipoxin; a Lipoxin analog; Lipoxin $A_4$; a Lipoxin $A_4$ analog; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeicosapentaenoic acid (HEPE); 15-HEPE; 12-HEPE; 5-HEPE; Annexin A1; a multi-region agent having a lipoxin region (see U.S. Pat. No. 5,441,951); aspirin-triggered lipid mediators, aspirin-triggered (ω-3) lipid mediators; 16-dimethyl-LXA$_4$; 15-epi-LXA$_4$; benzo-LXA$_4$ analogs; 9 (o-[9,12]-benzo-15-epi-LXA(4) methyl ester; and analogs or mimetics thereof. Lipid mediators and methods of producing them are described in, for example, U.S. Pat. Nos. 7,615,576; 5,441,951; 6,887,901; 7,737,178; 7,595,341; 7,378,444; 7,585,856; 6,703,423; 7,700,650; 7,812,054; 7,132,451; U.S. Patent Publications 2010/0105772; 2010/0105773; 2009/0156673; 2006/0293288; 2003/0166716 and 2008/0312323; and Serhan et al. FASEB Journal 2012 26.

In some embodiments, the agent can be an anti-infective agent or an antibiotic. The term "antibiotic" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and the like. Anti-infective agents can include, for example, antiviral and anti-fungal agents as well as agents for the treatment of parasitical infections.

In some embodiments, the agent can be an antinociceptive agent. As used herein "antinociceptive agent" refers to a compound which can reduce sensitivity to a painful stimulus. Antinociceptives are not limited by the mechanism of action. Non-limiting examples of antinociceptive agents include opiates (e.g. endorphins, enkephalins, and dynorphin), steroids, analgesics, barbiturates, oxycodone, morphine, lidocaine, and the like.

In some embodiments, an agent can be a chemotherapeutic agent. As used herein a "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

In some embodiments, the chemotherapeutic agent can be gemcitabine; fluorouracil, capecitabine; ciplastin; irinotecan; oxaliplatin; 5-fluorouracil; folinic acid; or erlotinib. In some embodiments, two or more chemotherapeutic agents can be administered, e.g. two agents, three agents or more agents. Multiple chemotherapeutic agents can be administered separately or concurrently. Non-limiting examples of chemotherapeutics which can be used in the methods described herein include cisplatin, doxorubicin, irinotecan (CPT11), paclitaxel, 5-fluorouracil (5-RU), capecitabine (XELODA™), 6-mercaptopurine, bevacizumab, methotrexate, 6-thioguanine, pemetrexed, raltitrexed, arabinosylcytosine ARA-C cytarabine (CYTOSAR-U®), dacarbazine (DTICDOME@), azocytosine, deoxycytosine, pyridmidene, fludarabine (FLUDARA®), cladrabine, and 2-deoxy-D-glucose. Further non-limiting examples of chemotherapeutic agents include of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, Ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gammall and calicheamicin omegall (see, e.g., Agnew, Chem Intl. Ed. Engl., 33: 183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, detorubicin, 6-diazo-5-oxoL-norleucine, ADRIAMYCIN® doxorubicin (including morpholinodoxorubicin, cyanomorpholino-doxorubicin, 2-pyrrolinodoxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin, folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formytransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSKS polysaccharide complex (JHS Natural Products, Eugene, Oreg.); razoxane; rhizoxin; sizofiran; spirogermanium; tenuazonic acid; triaziquone; 2,2', 2"trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophorfree, albumin-engineered nanoparticle formulation of paclitaxel (American Pharmaceutical Partners, Schaumberg, 111), and TAXOTERE® docetaxel (Rhone-Poulenc Rorer, Antony, France); chloranbucil; 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluoromethylomithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

In some embodiments, an agent can be a micronutrient. As used herein, the term "micronutrient" refers to vitamins or elements, usually in the form of minerals or metal salts, which are generally consumed in small amounts (e.g. less than 1 gm/day) and are absorbed unchanged. Micronutrients are essential for survival, growth, health, and reproduction. Non-limiting examples of micronutrients include calcium, phosphorus, potassium, iron, zinc, copper, magnesium, manganese, molybdenum, iodine, vitamin A, vitamin $B_2$, vitamin $B_6$, vitamin $B_9$, vitamin $B_{12}$, vitamin C, vitamin D, vitamin E, vitamin K, boron, ascorbic acid, calcium phosphate, salt, sodium chloride, and vitamin $D_3$.

In some embodiment, the particles described herein can comprise an imaging agent, for example, in order to allow visualization or detection of the particles themselves or to detect the extent and location of a region in an organism, for example, an inflammatory region in an organism. As used herein, the term "imaging agent" refers to an element or functional group in a molecule that allows for the detection, imaging, and/or monitoring of the presence and/or movement of a particle. The imaging agent can be an echogenic substance, non-metallic isotope, an optical reporter, a boron neutron absorber, a paramagnetic metal ion, a ferromagnetic metal, a gamma-emitting radioisotope, a positron-emitting radioisotope, or an x-ray absorber. Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N',N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p (2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 34-carboxy-pentyl)-3' ethyl-5,5'-dimethyloxacarbocyanine (CyA); 1H,5H,11H, 15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used. Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, Mol. Microbiol, 55:1767-1781 (2005), the GFP variant described in Crameri et al, Nat. Biotechnol., 14:315319 (1996), the cerulean fluorescent proteins described in Rizzo et al, Nat. Biotechnol, 22:445 (2004) and Tsien, Annu. Rev. Biochem., 67:509 (1998), and the yellow fluorescent protein described in Nagal et al, Nat. Biotechnol., 20:87-90 (2002). DsRed variants are described in, e.g., Shaner et al, Nat. Biotechnol., 22:1567-1572 (2004), and include mStrawberry, mCherry, morange, mBanana, mHoneydew, and mTangerine. Additional DsRed variants are described in, e.g., Wang et al, Proc. Natl. Acad. Sci. U.S.A., 101:16745-16749 (2004) and include mRaspberry and mPlum. Further examples of DsRed variants include mRFPmars described in Fischer et al, FEBS Lett., 577:227-232 (2004) and mRFPruby described in Fischer et al, FEBS Lett, 580:2495-2502 (2006). Suitable non-metallic isotopes include, but are not limited to, 11C, 14C, 13N, 18F, 123I, 124I, and 125I. Suitable radioisotopes include, but are not limited to, 99 mTc, 95Tc, 111In, 62Cu, 64Cu, Ga, 68Ga, and 153Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir. In some embodiments, the radionuclide is bound to a chelating agent or chelating agent-linker attached to the aggregate. Suitable radionuclides for direct conjugation include, without limitation, 18F, 124I, 125I, 131I, and mixtures thereof. Suitable radionuclides for use with a chelating agent include, without limitation, 47Sc, 64Cu, 67Cu, 89Sr, 86Y, 87Y, 90Y, 105Rh, 111Ag, 111In, 117mSn, 149Pm, 153Sm, 166Ho, 177Lu, 186Re, 188Re, 211At, 212Bi, and mixtures thereof. Suitable chelating agents include, but are not limited to, DOTA, BAD, TETA, DTPA, EDTA, NTA, HDTA, their phosphonate analogs, and mixtures thereof. In some embodiments, an imaging agent can be a MRI contrast dye or contrast agent. MRI contrast agents are well known in the art and include, by way of non-limiting example, gadolinium contrast agents (e.g. gadodiamide, gadobenic acid, gadopentetic acid); iron oxide contrast agents (e.g.

LUMIREM™); iron platimun contrast agents, manganese contrast agents, and PERFLUBRON™. One of skill in the art will be familiar with methods for attaching radionuclides, chelating agents, and chelating agent-linkers to the particles.

An imaging agent is detectable, either by observation or instrumentally. Specific devices or methods known in the art for the in vivo detection of fluorescence, e.g., from fluorophores or fluorescent proteins, include, but are not limited to, in vivo near-infrared fluorescence (see, e.g., Frangioni, *Curr. Opin. Chem. Biol*, 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, *IEEE Transactions on Biomedical Engineering*, 48:1034-1041 (2001), and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes. Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled aggregate. Positron emission tomography (PET) is another suitable technique for detecting radiation in a subject.

In some embodiments, an imaging agent can be used for tracking movement of a particle as described herein. An imaging agent used for this purpose can also be referred to as a "tracking agent."

The particles described herein can be caused to accumulate in certain locations or tissues in a subject by the addition of one or more targeting agents to the particle. A targeting agent preferentially binds to one or more tissues (e.g. lung or liver tissue) or locations that can otherwise be distinguished from the rest of the organism (e.g. a tumor or the site of inflammation). Thus, a particle comprising a targeting agent will bind to the desired tissue or location and a dose of particles will accumulate at that site. The use of targeting agents can increase efficacy, lower the total dose needed, and avoid side effects caused by the interaction of the particles or agents comprised by particles with tissues or locations not in need of treatment. In some embodiments, an agent can be a targeting agent. A targeting agent can be a peptide, a polypeptide, a protein, a peptidomimetic, a glycoprotein, a lectin, a nucleoside, a nucleotide, a nucleic acid, a monosaccharide, a disaccharide, a trisaccharide, an oligosaccharide, a polysaccharide, a lipopolysaccharide, a vitamin, a steroid, a hormone, a cofactor, a receptor, a receptor ligand, an antibody, an antigen binding fragment of an antibody, or an analog or derivative thereof. Examples of targeting agents suitable for targeting particles to sites of inflammation (e.g. autoimmune disorders or arthritis) include, but are not limited to agents binding or bound by a molecule selected from the group consisting of VACM-1; fibrin, integrin, AR-A1, (see, Lewis et al. Nanomed Nanobiotechnol 2011 3:400-420; which is incorporated by reference in its entirety herein).

In some embodiments, a particle can comprise at least one agent, e.g. one agent, two agents, three agents, four agents, or more agents. In some embodiments, a particle can comprise multiple agents of the same type, e.g. two lipid mediators such as a resolvin and a neuroprotectin. In some embodiments, a particle can comprise multiple types of agents, e.g. a targeting agent and a therapeutic agent. In some embodiments, a particle can comprise a targeting agent and a therapeutic agent. In some embodiments, a particle can comprise a targeting agent and an imaging agent. In some embodiments, a particle can comprise a targeting agent and a micronutrient. In some embodiments, a particle can comprise a targeting agent and a tracking agent. In some embodiments, a particle can comprise a targeting agent and a chemotherapeutic agent. In some embodiments, a particle can comprise a targeting agent and a lipid mediator.

In some embodiments, an agent can be located on the surface of a particle. In some embodiments, an agent can be located in the lipid bilayer of a particle. In some embodiments, an agent can be located in the interior space of a particle. In some embodiments, an agent can be located in the aqueous interior of a particle.

In some embodiments, the agent can comprise 0.01 wt % to 99 wt % of the particle. In some embodiments, $10^5$ particles can comprise from about 0.01 ng to 100 ng of the agent. In some embodiments, $10^5$ particles can comprise from about 0.1 ng to about 10 ng of the agent. In some embodiments, $10^5$ particles can comprise from about 1 ng to about 50 ng of the agent. In some embodiments, $10^5$ particles can comprise from about 5 ng to about 15 ng of the agent.

In some embodiments, the particle can be of a size from about 1 nm to about 1.5 µm in diameter. In some embodiments, the particle can be of a size from about 10 nm to about 1 µm in diameter. In some embodiments, the particle can be of a size from about 100 nm to about 1 µm in diameter. In some embodiments, the particle can be of a size from about 100 nm to about 0.5 µm in diameter. In some embodiments, the particle can be of a size from about 150 nm to about 250 nm in diameter. In some embodiments, the particle can be of a size from about 450 nm to about 550 nm in diameter. In some embodiments, the particle can be of a size of about 200 nm in diameter. In some embodiments, the particle can be of a size of about 500 nm in diameter. In some embodiments, the particle can be of a size of about 1100 nm in diameter.

The technology described herein relates to methods of making particles as described above herein. The methods of making particles described herein utilize cellular-derived microparticles as a starting material. Sources and varieties of cellular-derived microparticles are described above herein. In some embodiments, the microparticles can be purified or separated from, for example, cellular debris or culture media. Methods of purifying microparticles are well known in the art and are described above herein. In some embodiments, the method of preparing a particle comprises providing a cellular-derived microparticle and sonicating the microparticle in the presence of at least one agent.

In some embodiments, the cellular-derived microparticles can be obtained from a sample obtained from a subject. In some embodiments, the sample obtained from a subject can be a blood sample. In some embodiments, the blood sample can comprise leukocytes. In some embodiments, leukocytes in a sample obtained from a subject can be contacted with a leukocyte agonist to generate cellular-derived microparticles. Leukocyte agonists are described above herein. In some embodiments, the leukocytes in a sample obtained from a subject can be isolated or enriched prior to being contacted with a leukocyte agonist.

Methods of sonicating a sample are well known in the art and apparatuses for sonication are commercially available, e.g. the Q125 (Cat No. Q125; Qsonica; Newtown, Conn.) or Cat No; WU-04711-35 from Cole-Palmer (Vernon Hill, Ill.). In some embodiments, sonication can occur at from about 1 to about 100 W. In some embodiments, sonication can occur at from about 5-50 W. In some embodiments, sonication can occur at from about 10-20 W. In some embodiments, sonication can occur at about 15 W. In some embodiments, sonication can last from 30 seconds to 3 hours. In some embodiments, sonication can last from 1 minute to 1 hour. In some embodiments, sonication can last from 10 minutes to 20 minutes. In some embodiments, sonication can last about 15 minutes.

In some embodiments, the microparticle prepared according to the methods described herein can comprise at least one component of a cellular-derived microparticle. Various components of cellular-derived microparticles are described above herein.

In some embodiments, a particle prepared according to the methods described herein can comprise at least one agent. Agents suitable for use in the methods and compositions of the technology described herein are themselves described above herein. One method of incorporating an agent into a particle as described herein is to add the agent to a suspension of microparticles prior to sonication. In some embodiments, an agent is added to a suspension of cellular-derived microparticles prior to sonication. In some embodiments, an agent is added to a suspension of cellular-derived microparticles during sonication. In some embodiments, multiple agents are added to a suspension of cellular-derived microparticles prior to sonication. In some embodiments, multiple agents are added to a suspension of cellular-derived microparticles during sonication. Multiple agents can be added at the same time or in a step-wise manner. In some embodiments, a first agent is added to a suspension of cellular-derived microparticles and incorporated via sonication and a second agent is then added to the suspension of particles and incorporated via sonication, e.g. there are two rounds of sonication. The incorporation of agents can be monitored as described above herein.

In some embodiments, following the generation of particles, the particles can be purified, isolated, or enriched. In some embodiments, particles of a desired size or range of sizes can be selected by separating the desired particles from particles of other sizes and/or other components of a suspension. Non-limiting means of selecting a particle of a desired size or range of sizes include filtration, centrifugation, gel filtration, gel filtration chromatography, gel permeation chromatography, size-exclusion chromatography, and flow cytometry. For example, particles can be centrifuged to separate them from heavier or lighter components of a suspension. Alternatively, the particles can be subjected to, e.g. a size exclusion chromatography column. By way of non-limiting example, the particles can be run over a Sephadex G50 column (Cat No. G50150; Sigma-Aldrich; St. Louis, Mo.) and fractions collected in 0.2 µm-filtered DPBS. In some embodiments, the size of the purified, isolated, or enriched particles can be confirmed, e.g. by using flow cytometry and calibration beads or electron microscopy.

In some embodiments, the method of preparing a particle can comprise selecting a particle(s) of from about 1 nm to about 1.5 µm in diameter. In some embodiments, the method of preparing a particle can comprise selecting a particle(s) of from about 10 nm to about 1 µm in diameter. In some embodiments, the method of preparing a particle can comprise selecting a particle(s) of from about 100 nm to about 1 µm in diameter. In some embodiments, the method of preparing a particle can comprise selecting a particle(s) of from about 100 nm to about 0.5 µm in diameter. In some embodiments, the method of preparing a particle can comprise selecting a particle(s) of from about 150 nm to about 250 nm in diameter. In some embodiments, the method of preparing a particle can comprise selecting a particle(s) of from about 450 nm to about 550 nm in diameter. In some embodiments, the method of preparing a particle can comprise selecting a particle(s) of about 200 nm in diameter. In some embodiments, the method of preparing a particle can comprise selecting a particle(s) of about 500 nm in diameter. In some embodiments, the method of preparing a particle can comprise selecting a particle(s) of about 1100 nm in diameter.

In some embodiments, the agent can comprise 0.01 wt % to 99 wt % of the particle. In some embodiments, $10^5$ particles can comprise from about 0.01 ng to 100 ng of the agent. In some embodiments, $10^5$ particles can comprise from about 0.1 ng to about 10 ng of the agent. In some embodiments, $10^5$ particles can comprise from about 1 ng to about 50 ng of the agent. In some embodiments, $10^5$ particles can comprise from about 5 ng to about 15 ng of the agent.

In some embodiments, the method of preparing a particle described herein further comprises determining the effectiveness of a particle by performing a tissue regeneration assay. A tissue regeneration assay can comprise the use of any organism, wherein a portion of a tissue is damaged or removed. A particle as described herein is then administered to the organism and the rate of tissue regeneration is determined. The rate of tissue regeneration can be compared to the rate observed when an organism is administered a control or is not treated. Other parameters that can be determined during a tissue regeneration assay include, but are not limited to, symptoms or outcomes such as pain, markers of pain, signs or symptoms of inflammation, final degree of regeneration, and quality of regeneration. In some embodiments, a tissue regeneration assay can be a Platyhelminthes tissue regeneration assay (see, e.g. Serhan et al. FASEB Journal 2012-201442). Briefly, the head of a planaria can be resected and the time required for the head to regenerate and/or the rate of regeneration determined. Planaria can be maintained in water or water comprising the particle to be tested in the assay. The rate of regeneration can be quantified using photographical techniques to determine the size of the planaria.

In some embodiments, a pharmaceutical composition can comprise a particle as described herein, and optionally a pharmaceutically acceptable carrier. The compositions encompassed by the invention can further comprise at least one pharmaceutically acceptable excipient.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the particle.

As described in detail below, the pharmaceutical compositions of the present invention comprising a particle as described herein can be specially formulated for administration to a subject in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, a particle can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred. The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. The dosage may be determined by a physician and adjusted, as necessary, to suit observed effects of the treatment.

In certain embodiments, the effective dose of a composition comprising a particle as described herein can be administered to a patient once. In certain embodiments, the effective dose of a composition comprising a particle can be administered to a patient repeatedly. Patients can be administered a therapeutic amount of a composition comprising a particle, such as 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg or 50 mg/kg. A composition comprising a particle can be administered over a period of time, such as over a 5 minute, 10 minute, 15 minute, 20 minute, or 25 minute period. The administration is repeated, for example, on a regular basis, such as hourly for 3 hours, 6 hours, 12 hours or longer or such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of a composition comprising a particle can reduce levels of a marker or symptom of, for example, inflammation (e.g., swelling or redness) by at least 10%, at least 15%, at least 20%, at least 25%, at least 30%, at least 40%, at least 50%, at least 60%, at least 70%, at least 80% or at least 90% or more.

The dosage of a particle as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such subdoses can be administered as unit dosage forms. In some embodiments, administration can be chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

As disclosed herein, a particle can be administered to a subject alone, or optionally in combination (e.g. simultaneously with, sequentially or separately) with one or more pharmaceutically active agents, e.g. a second therapeutic agent known to be beneficial in treating, for example, inflammation. For example, exemplary pharmaceutically active compound include, but are not limited to, those found in *Harrison's Principles of Internal Medicine*, $18^{th}$ Edition, Eds. A. Fauci et al. McGraw-Hill N.Y., NY; Physicians' Desk Reference, $65^{th}$ Edition, 2011, Oradell, N.J., Medical Economics Co.; Pharmacological Basis of Therapeutics, 12$^{th}$ Edition, Brunton et al., 2010; United States Pharmacopeia, The National Formulary, USP XXXIV NF XIX, 2011; current edition of Goodman and Gilman's *The Pharmacological Basis of Therapeutics*; and current edition of *The Merck Index*, the complete contents of all of which are incorporated herein by reference. By way of non-limiting example, pharmaceutically active compounds useful in treating inflammation include, non-steroidal anti-inflammatory drugs (NSAIDs—such as aspirin, ibuprofen, or naproxen); coricosteroids (such as presnisone); anti-malarial medication (such as hydrochloroquine); methotrexrate; sulfasalazine; leflunomide; anti-TNF medications; cyclophosphamise; and mycophenolate.

In some embodiments, a composition comprising a particle as described herein and a pharmaceutically active agent can be administered to the subject in the same pharmaceutical composition or in different pharmaceutical compositions (at the same time or at different times). When administered at different times, a composition comprising a particle and the additional pharmaceutically active agent can be administered within 5 minutes, 10 minutes, 20 minutes, 60 minutes, 2 hours, 3 hours, 4, hours, 8 hours, 12 hours, 24 hours of administration of the other. When a composition comprising a particle and the pharmaceutically active agent are administered in different pharmaceutical compositions, routes of administration can be different. For example, a composition comprising a particle can be administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration, and the pharmaceutically active agent is administered by a different route, e.g. a route commonly used in the art for administration of the pharmaceutically active agent. In some embodiments, a composition comprising a particle can precede, can be co-current with and/or follow the pharmaceutically active agent by intervals ranging from minutes to weeks. In embodiments where a composition comprising a particle and a pharmaceutically active agent are applied separately to a cell, tissue or organism, one would generally ensure that a significant period of time did not expire between the time of each delivery, such that the composition comprising a particle and a pharmaceutically active agent would still be able to exert an advantageously combined effect on the cell, tissue or organism.

In some embodiments, the invention contemplates the use of a composition comprising a particle and the practice of the methods described herein in conjunction with other therapies such as, for example, surgery.

A pharmaceutical composition comprising a particle as described herein can be administered to a subject by various routes, including, but not limited to, orally, by injection, transdermally, by direct application (e.g. to the skin or eye or to tissue exposed by, for example, surgery or injury), subcutaneous, intravenous (including bolus injection), intramuscular, intrathecal, and intraarterial.

In some embodiments, the pharmaceutical composition comprising a particle as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the particle as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a particle as disclosed herein can also be incorporated into the parenteral dosage forms of the disclosure, including conventional and controlled-release parenteral dosage forms.

In some embodiments, the particle can be administered to a subject topically. In some embodiments, topical dosage forms of the particle include, but are not limited to, creams, lotions, ointments, gels, shampoos, sprays, aerosols, solutions, emulsions, and other forms known to one of skill in the art. See, e.g., Remington: The Science and Practice of Pharmacy, 21st Ed., Lippincott, Williams, and Wilkins, Philadelphia Pa. (2005); and Ansel's Pharmaceutical Dosage Forms and Drug Delivery Systems, 9$^{th}$ Ed., Lippincott, Williams, and Wilkins, Philadelphia, Pa. (2011). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington: The Science and Practice of Pharmacy, 21st Ed., Lippincott, Williams, and Wilkins, Philadelphia Pa. (2005).

Transdermal and mucosal dosage forms of the compositions comprising a modulator of a particle as disclosed herein include, but are not limited to, ophthalmic solutions, patches, sprays, aerosols, creams, lotions, suppositories, ointments, gels, solutions, emulsions, suspensions, or other forms known to one of skill in the art. See, e.g., Remington: The Science and Practice of Pharmacy, 21st Ed., Lippincott, Williams, and Wilkins, Philadelphia Pa. (2005); and Ansel's Pharmaceutical Dosage Forms and Drug Delivery Systems, 9$^{th}$ Ed., Lippincott, Williams, and Wilkins, Philadelphia, Pa. (2011). Dosage forms suitable for treating mucosal tissues within the oral cavity can be formulated as mouthwashes, as oral gels, or as buccal patches. Additional transdermal dosage forms include "reservoir type" or "matrix type"

patches, which can be applied to the skin and worn for a specific period of time to permit the penetration of a desired amount of active ingredient.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with a particle. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent.

Pharmaceutical compositions comprising a particle can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In some embodiments, a particle as described herein can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, a particle as described herein can be administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administration is particularly preferred when the respiratory disorder occurs continuously in the subject, for example where the subject has continuous symptoms of a respiratory disorder. Each pulse dose can be reduced and the total amount of drug administered over the course of treatment to the patient is minimized. In some embodiments, individual pulses can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours.

In some embodiments, an interval between pulses or an interval of no delivery is greater than 24 hours and preferably greater than 48 hours, and can be for even longer such as for 3, 4, 5, 6, 7, 8, 9 or 10 days, two, three or four weeks or even longer. As the results achieved may be surprising, the interval between pulses, when necessary, can be determined by one of ordinary skill in the art. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life.

In some embodiments, the number of pulses in a single therapeutic regimen may be as little as two, but is typically from about 5 to 10, 10 to 20, 15 to 30 or more. In fact, patients can receive drugs for life according to the methods of this invention without the problems and inconveniences associated with current therapies. Compositions can be administered by most any means, but are preferable delivered to the patient as an injection (e.g. intravenous, subcutaneous, and intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590. Sustained release can also be accomplished by means of an osmotic pump. In some embodiments, a particle is administered over a period of several days, such as 2, 3, 4, 5, 6 or 7 days.

In some embodiments, the technology described herein relates to methods comprising administering a particle as described herein, or composition comprising a particle, to a subject. In some embodiments, the subject is in need of a treatment for a disease or disorder. In some embodiments, a particle can be administered to a subject in need of treatment for inflammation. In some embodiments, the particle can be administered to a subject in need of treatment for a condition not associated with inflammation.

In some embodiments, the particle(s) administered to the subject are autologous, e.g. the particle was prepared using cellular-derived microparticles produced from the subject's cells or cells obtained from the subject.

In some embodiments, the subject can be administered a therapeutically effective amount of a particle. In some embodiments, the subject can be administered a therapeutically effective amount of a particle comprising an agent. In some embodiments, the subject can be administered a therapeutically effective amount of an agent. In some embodiments, the particle comprises a therapeutically effective amount of an agent.

In some embodiments, the technology described herein relates to methods of treating inflammation and/or promoting wound healing in a subject. In some embodiments, the technology described herein relates to methods of treating a subject in need of treatment for inflammation, wound healing, or pain management. A "subject in need" of treatment for a particular condition can be a subject having that condition, diagnosed as having that condition, or at risk of developing that condition.

As used herein, "inflammation" refers to the complex biological response to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), and chemokines that chemoattract inflammatory cells. Inflammation can include both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

An inflammatory condition is any disease state characterized by inflammatory tissues (for example, infiltrates of leukocytes such as lymphocytes, neutrophils, macrophages, eosinophils, mast cells, basophils and dendritic cells) which provoke or contribute to the abnormal clinical and histological characteristics of the disease state. Inflammatory conditions include, but are not limited to, inflammatory conditions of the skin, inflammatory conditions of the lung, inflammatory conditions of the joints, inflammatory conditions of the gut, inflammatory conditions of the eye, inflammatory conditions of the endocrine system, inflammatory conditions of the cardiovascular system, inflammatory conditions of the kidneys, inflammatory conditions of the liver, inflammatory conditions of the central nervous system, or sepsis-associated conditions, in some embodiments, the inflammatory condition is associated with wound healing. Inflammation is often part of the wound and/or tissue healing process and the methods and compositions described herein can be used to enhance or promote wound and/or tissue healing, in some embodiments, the inflammatory condition is a temporomandibular joint disorder.

In some embodiments, the inflammation to be treated according to the methods described herein can be skin inflammation; inflammation caused by substance abuse or drug addiction; inflammation associated with infection; inflammation of the cornea; inflammation of the retina; inflammation of the spinal cord; inflammation associated with organ regeneration; and pulmonary inflammation. In some embodiments, a subject in need of treatment for inflammation, wound healing, or pain management can be a subject having, or diagnosed as having temporomandibular joint disorders; COPD; smoke-induced lung injury; renal dialysis associated disorders; spinal cord injury; graft vs. host disease; bone marrow transplant or complications thereof; infection; trauma; pain; incisions; surgical incisions; a chronic pain disorder; a chronic bone disorder; mastitis; and joint disease. In some embodiments, trauma can include battle-related injuries or tissue damage occurring during a surgery. Smoke-induced lung injury can result from exposure to tobacco smoke, environmental pollutants (e.g. smog or forest fires), or industrial exposure.

By way of non-limiting example, inflammatory conditions can be inflammatory conditions of the skin, such as Sweet's syndrome, pyoderma gangrenosum, subcorneal pustular dermatosis, erythema elevatum diutinum, Behcet's disease or acute generalized exanthematous pustulosis, a bullous disorder, psoriasis, a condition resulting in pustular lesions, acne, acne vulgaris, dermatitis (e.g., contact dermatitis, atopic dermatitis, seborrheic dermatitis, eczematous dermatitides, eczema craquelee, photoallergic dermatitis, phototoxicdermatitis, phytophotodermatitis, radiation dermatitis, stasis dermatitis or allergic contact dermatitis), eczema, ulcers and erosions resulting from trauma, burns, ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin, cutaneous atrophy resulting from the topical use of corticosteroids, and inflammation of mucous membranes (e.g. cheilitis, chapped lips, nasal irritation, mucositis and vulvovaginitis).

By way of non-limiting example, inflammatory conditions can be inflammatory conditions of the lung, such as asthma, bronchitis, chronic bronchitis, bronchiolitis, pneumonia, sinusitis, emphysema, adult respiratory distress syndrome, pulmonary inflammation, pulmonary fibrosis, and cystic fibrosis (which may additionally or alternatively involve the gastro-intestinal tract or other tissue(s)).

By way of non-limiting example, inflammatory conditions can be inflammatory conditions of the joints, such as rheumatoid arthritis, rheumatoid spondylitis, juvenile rheumatoid arthritis, osteoarthritis, gouty arthritis, infectious arthritis, psoriatic arthritis, and other arthritic conditions.

By way of non-limiting example, inflammatory conditions can be inflammatory conditions of the gut or bowel, such as inflammatory bowel disease, Crohn's disease, ulcerative colitis and distal proctitis By way of non-limiting example, inflammatory conditions can be inflammatory conditions of the eye, such as dry eye syndrome, uveitis (including iritis), conjunctivitis, scleritis, and keratoconjunctivitis sicca By way of non-limiting example, inflammatory conditions can be inflammatory conditions of the endocrine system, such as autoimmune thyroiditis (Hashimoto's disease), Graves' disease, Type I diabetes, and acute and chronic inflammation of the adrenal cortex.

By way of non-limiting example, inflammatory conditions can be inflammatory conditions of the cardiovascular system, such as coronary infarct damage, peripheral vascular disease, myocarditis, vasculitis, revascularization of stenosis, artherosclerosis, and vascular disease associated with Type II diabetes.

By way of non-limiting example, inflammatory conditions can be inflammatory conditions of the kidneys, such as glomerulonephritis, interstitial nephritis, lupus nephritis, and nephritis secondary to Wegener's disease, acute renal failure secondary to acute nephritis, post-obstructive syndrome and tubular ischemia.

By way of non-limiting example, inflammatory conditions can be inflammatory conditions of the liver, such as hepatitis (arising from viral infection, autoimmune responses, drug treatments, toxins, environmental agents, or as a secondary consequence of a primary disorder, biliary atresia, primary biliary cirrhosis and primary sclerosing cholangitis.

By way of non-limiting example, inflammatory conditions can be inflammatory conditions of the central nervous system, such as multiple sclerosis and neurodegenerative diseases such as Alzheimer's disease or dementia associated with HIV infection.

By way of non-limiting example, inflammatory conditions can be inflammatory conditions of the central nervous system, such as MS; all types of encephalitis and meningitis; acute disseminated encephalomyelitis; acute transverse myelitis; neuromyelitis optica; focal demyelinating syndromes (e.g., Balo's concentric sclerosis and Marburg variant of MS); progressive multifocal leukoencephalopathy; subacute sclerosing panencephalitis; acute haemorrhagic leucoencephalitis (Hurst's disease); human T-lymphotropic virus type-1 associated myelopathy/tropical spactic paraparesis; Devic's disease; human immunodeficiency virus encephalopathy; human immunodeficiency virus vacuolar myelopathy; peipheral neuropathies; Guillame-Barre Syndrome and other immune mediated neuropathies; and myasthenia gravis.

By way of non-limiting example, inflammatory conditions can be sepsis-associated conditions, such as systemic inflammatory response syndrome (SIRS), septic shock or multiple organ dysfunction syndrome (MODS).

Further non-limiting examples of inflammatory conditions include, endotoxin shock, periodontal disease, polychondritis; periarticular disorders; pancreatitis; system lupus erythematosus; Sjogren's syndrome; Behcet's Syndrome; vasculitis sarcoidosis amyloidosis; allergies; anaphylaxis; systemic mastocytosis; pelvic inflammatory disease; multiple sclerosis; multiple sclerosis (MS); celiac disease, Guillain-Barre syndrome, sclerosing cholangitis, autoimmune hepatitis, Raynaud's phenomenon, Goodpasture's syndrome, Wegener's granulomatosis, polymyalgia rheumatica, temporal arteritis/giant cell arteritis, chronic fatigue syndrome CFS), autoimmune Addison's Disease, ankylosing spondylitis, Acute disseminated encephalomyelitis, antiphospholipid antibody syndrome, syndrome, optic neuritis, Ord's thyroiditis, pemphigus, pernicious anaemia, polyarthritis in dogs, Reiter's syndrome, Takayasu's arteritis, warm autoimmune hemolytic anemia, fibromyalgia (FM), autoinflammatory PAPA syndrome, Familial Mediterranean Fever, polymyalgia rheumatica, polyarteritis nodosa, churg strauss syndrome fibrosing alveolitis, hypersensitivity pneumonitis, allergic aspergillosis, cryptogenic pulmonary eosinophilia, bronchiolitis obliterans organising pneumonia; urticaria; lupoid hepatitis; familial cold autoinflammatory syndrome, Muckle-Wells syndrome, the neonatal onset multisystem inflammatory disease, graft rejection (including allograft rejection and graft-v-host disease), otitis, chronic obstructive pulmonary disease, sinusitis, chronic prostatitis, reperfusion injury, silicosis, inflammatory myopathies, hypersensitivities and migraines. In some embodiments, an inflammatory condition is associated with an infection, e.g. viral, bacterial, fungal, parasite or prion infections, in some embodiments, an inflammatory condition is associated with an allergic response. In some embodiments, an inflammatory condition is associated with a pollutant (e.g. asbestosis, silicosis, or berylliosis).

In some embodiments, the inflammation is associated with a wound. In some embodiments, the technology described herein relates to methods of promoting wound healing. As used herein, "wound" refers broadly to injuries to an organ or tissue of an organism that typically involves division of tissue or rupture of a membrane (e.g., skin), due to external violence, a mechanical agency, or infectious disease. A wound can be an epithelial, endothelial, connective tissue, ocular, or any other kind of wound in which the strength and/or integrity of a tissue has been reduced, e.g. trauma has caused damage to the tissue. The term "wound" encompasses injuries including, but not limited to, lacerations, abrasions, avulsions, cuts, burns, velocity wounds (e.g., gunshot wounds), penetration wounds, puncture wounds, contusions, diabetic wounds, hematomas, tearing wounds, and/or crushing injuries. In one aspect, the term "wound" refers to an injury to the skin and subcutaneous tissue initiated in any one of a variety of ways (e.g., pressure sores from extended bed rest, wounds induced by trauma, cuts, ulcers, burns and the like) and with varying characteristics. As used herein, the term "wound healing" refers to a process by which the body of a wounded organism initiates repair of a tissue at the wound site (e.g., skin). The wounds healing process requires, in part, angiogenesis and revascularization of the wounded tissue. Wound healing can be measured by assessing such parameters as contraction, area of the wound, percent closure, percent closure rate, and/or infiltration of blood vessels as known to those of skill in the art. In some embodiments, the particles and compositions described herein can be applied topically to promote wound healing.

In some embodiments, the technology described herein relates to methods of treating dermatological conditions. Dermatological conditions can include skin wounds, inflammation of the skin, and/or inflammatory conditions of the skin. In some embodiments, the particles and compositions described herein can be applied topically to treat a dermatological condition.

Pain can be a symptom of or an effect of inflammation. Accordingly, reducing inflammation and/or promoting the resolution of inflammation can reduce or manage pain in a subject. In some embodiments, a particle can comprise an antinociceptive agent which can reduce or manage pain through an effect independent of anti-inflammatory activity. In some embodiments, the technology described herein relates to methods of treating a subject for pain, or for methods of pain management.

Administration according to the methods described herein can be, for example, by injection, by infusion, by instillation, by inhalation, by ingestions, or by topical application. Administration can be local and/or systemic.

Some embodiments of the present invention can be defined as any of the following numbered paragraphs.
1. A particle comprising at least one component of a cellular-derived microparticle and at least one agent.
2. The particle of paragraph 1, wherein the cellular-derived microparticle is a microparticle generated during the initiation phase of an acute inflammatory response.
3. The particle of any of paragraphs 1-2, wherein the cellular-derived microparticle is generated in vitro by cellular activation and has a pro-resolving microparticle phenotype.
4. The particle of paragraph 3, wherein the pro-resolving microparticle generated in vitro is a microparticle generated by contacting a cell with a leukocyte agonist.
5. The method of paragraph 4, wherein the leukocyte agonist is selected from the group consisting of:
   IL-8; fMLP; IL-4; zymosan; LPS; leukotriene B4; and C5a.
6. The particle of any of paragraphs 1-5, wherein the cellular-derived microparticle is a microparticle derived from leukocytes.
7. The particle of any of paragraphs 1-6, wherein the cellular-derived microparticle is a microparticle derived from mammalian leukocytes.
8. The particle of any of paragraphs 1-7, wherein the cellular-derived microparticle is a microparticle derived from human leukocytes.
9. The particle of any of paragraphs 1-8, wherein the at least one component of a cellular-derived microparticle is selected from the group consisting of:
   a hydroxy-docoshexaeonic acid (HDHA); 17-HDHA; 14-HDHA; 13-HDHA; 7-HDHA; 4-HDHA; a hydroxyl-eicostatentraenoic acid; a eicosanoid prostaglandin; a hydroxyl-eicosapentaenoic acid; and any combination thereof.
10. The particle of any of paragraphs 1-9, wherein the at least one component of a cellular-derived microparticle is selected from the group consisting of:
    Resolvin D1; Resolvin D2; Resolvin D3; Resolvin D5; Resolvin D6; Maresin 1; Protectin D1; Lipoxin $A_4$; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; and 5-HEPE.
11. The particle of any of paragraphs 1-10, wherein the agent is a therapeutic agent, an imaging agent, a micronutrient, a targeting agent, a tracking agent, or a chemotherapeutic agent.
12. The particle of any of paragraphs 1-11, wherein the agent is selected from the group consisting of small organic or inorganic molecules; saccharines; oligosaccharides; polysaccharides; lipids, biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof.
13. The particle of any of paragraphs 1-12, wherein the agent is a lipid mediator.
14. The particle of paragraph 14, wherein the lipid mediator is selected from the group consisting of a Resolvin; Resolvin D1; Resolvin D2; Resolvin D3; Resolvin D5; Resolvin D6; aspirin-triggered Resolvin; aspirin-triggered Resolvin D1; aspirin-triggered Resolvin D2; aspirin-triggered Resolvin D3; Maresin 1; Protectin D1; 17-HDHA; 14-HDHA; 13-HDHA; 7-HDHA; 4-HDHA; a Lipoxin; a Lipoxin analog; Lipoxin $A_4$; a Lipoxin $A_4$ analog; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; 5-HEPE; Annexin A1; and analogs or mimetics thereof.
15. The particle of any of paragraphs 1-14, wherein the agent is a therapeutic agent selected from the group consisting of anti-inflammatory agents, anti-infective agents, antibiotics, pro-resolving drugs; and antinociceptives.
16. The particle of paragraph 15, wherein the therapeutic agent is selected from the group consisting of:
    nonsteroidal anti-inflammatory drugs; glucocorticoids, CO-donor compounds, and NO-donor compounds.
17. The particle of any of paragraphs 1-16, wherein the agent is an imaging agent selected from the group consisting of a fluorescent dye; a fluorescent imaging agent; a radioisotope; and a MRI contrast agent.
18. The particle of any of paragraphs 1-17, wherein the agent is a targeting agent selected from the group consisting of peptides, polypeptides, proteins, peptidomimetics, glycoproteins, lectins, nucleosides, nucleotides, nucleic acids, monosaccharides, disaccharides, trisaccharides, oligosaccharides, polysaccharides, lipopolysaccharides, vitamins, steroids, hormones, cofactors, receptors, receptor ligands, antibodies, antigen binding fragments of antibodies, and analogs and derivatives thereof.
19. The particle of any of paragraphs 1-18, wherein the particle comprises both a targeting agent and at least one of a therapeutic agent, an imaging agent, a micronutrient, a tracking agent, or a chemotherapeutic agent.
20. The particle of any of paragraphs 1-19, wherein the agent comprises about 0.01 wt % to about 99 wt % of the particle.
21. The particle of any of paragraphs 1-20, wherein $10^5$ particles comprise from about 0.01 ng to about 100 ng of the agent.
22. The particle of paragraph 21, wherein $10^5$ particles comprise from about 5 ng to about 15 ng of the agent.
23. The particle of any of paragraphs 1-22, wherein the particle is of a size from about 100 nm to about 1.5 μm in diameter.
24. The particle of paragraph 23, where in the particle is of a diameter selected from the group consisting of: about 200 nm; about 500 nm; and about 1100 nm.
25. A method of preparing a particle comprising:
providing a cellular-derived microparticle; and
sonicating the microparticle in the presence of at least one agent.
26. The method of paragraph 25, wherein the sonication occurs at 1 to 100 W.
27. The method of paragraph 26, wherein the sonication occurs at about 15 W.
28. The method of any of paragraphs 25-27, wherein the cellular-derived microparticle is a microparticle derived from leukocytes.
29. The method of any of paragraphs 25-28, wherein the cellular-derived microparticle is a microparticle derived from mammalian leukocytes.
30. The method of any of paragraphs 25-29, wherein the cellular-derived microparticle is a microparticle derived from human leukocytes.
31. The method of any of paragraphs 25-30, wherein the cellular-derived microparticles are obtained from a subject's blood sample.
32. The method of any of paragraphs 25-31, further comprising contacting leukocytes in a sample obtained from a subject with a leukocyte agonist.
33. The method of any of paragraphs 25-32, wherein the cellular-derived microparticle is a microparticle generated during the initiation phase of an acute inflammatory response.
34. The method of any of paragraphs 25-33, wherein the cellular-derived microparticle is generated in vitro by cellular activation and has a pro-resolving microparticle phenotype.
35. The method of paragraph 34, wherein the pro-resolving microparticle generated in vitro is a microparticle generated by contacting a cell with a leukocyte agonist.
36. The method of paragraph 32 or 35, wherein the leukocyte agonist is selected from the group consisting of:
IL-8; fMLP; IL-4; zymosan; LPS; leukotriene B4; and C5a.
37. The method of any of paragraphs 25-36, further comprising a step selected from the group consisting of: filtration, centrifugation, or combination thereof, thereby selecting particles of desired size.
38. The method of any of paragraphs 25-37, further comprising selecting the particle of size from about 100 nm to about 1.5 μm.
39. The method of any of paragraphs 25-38, further comprising selecting the particle of size from about 200 nm, about 500 nm, or about 1100 nm.
40. The method of any of paragraphs 25-39, wherein the particle comprises at least one component of a cellular-derived microparticle selected from the group consisting of:
a hydroxy-docoshexaeonic acid (HDHA); 17-HDHA; 14-HDHA; 13-HDHA; 7-HDHA; 4-HDHA; a hydroxyl-eicostatentraenoic acid; a eicosanoid prostaglandin; a hydroxyl-eicosapentaenoic acid; and any combination thereof.
41. The method of any of paragraphs 25-40, wherein the particle comprises at least one component of a cellular-derived microparticle selected from the group consisting of:
Resolvin D1; Resolvin D2; Resolvin D3; Resolvin D5; Resolvin D6; Maresin 1; Protectin D1; Lipoxin $A_4$; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; and 5-HEPE.
42. The method of any of paragraphs 25-41, wherein the agent is selected from the group consisting of:
a therapeutic agent, an imaging agent, a micronutrient, a targeting agent, a tracking agent, a chemotherapeutic agent.
43. The method of any of paragraphs 25-42, wherein the agent is selected from the group consisting of small organic or inorganic molecules; saccharines; oligosaccharides; polysaccharides; lipids, biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof.
44. The method of any of paragraphs 25-43, wherein the agent is a lipid mediator.
45. The method of paragraph 44, wherein the lipid mediator is selected from the group consisting of:
a Resolvin; Resolvin D1; Resolvin D2; Resolvin D3; Resolvin D5; Resolvin D6; aspirin-triggered Resolvin; aspirin-triggered Resolvin D1; aspirin-triggered Resolvin D2; aspirin-triggered Resolvin D3; Maresin 1; Protectin D1; 17-HDHA; 14-HDHA; 13-HDHA; 7-HDHA; 4-HDHA; a Lipoxin; a Lipoxin analog; Lipoxin $A_4$; a Lipoxin $A_4$ analog; Lipoxin $B_4$; 5,15-dihydroxyeicosatetraenoic acid; Prostaglandin $D_2$; Prostaglandin $E_2$; Prostaglandin $F_{2a}$; Thromboxane $B_2$; 15-hydroxyeicosatetraenoic acid (HETE); 12-HETE; 11-HETE; 5-HETE; Resolvin E2; Lipoxin $A_5$; Lipoxin $B_5$; 5,15-dihydroxyeicosapentaenoic acid; 18-hydroxyeciosapentaenoic acid (HEPE); 15-HEPE; 12-HEPE; 5-HEPE; Annexin A1; and analogs or mimetics thereof.
46. The method of any of paragraphs 25-45, wherein the therapeutic agent is selected from the group consisting of anti-inflammatory agents, anti-infective agents, antibiotics, pro-resolving drugs; and antinociceptives.

47. The method of any of paragraphs 25-46, wherein the therapeutic agent is selected from the group consisting of nonsteroidal anti-inflammatory drugs; glucocorticoids, CO-donor compounds, and NO-donor compounds.

48. The method of any of paragraphs 25-47, wherein the agent is an imaging agent selected from the group consisting of
a fluorescent dye; a fluorescent imaging agent; a radioisotope; and a MRI contrast agent.

49. The method of any of paragraphs 25-48, wherein the agent is a targeting agent selected from the group consisting of peptides, polypeptides, proteins, peptidomimetics, glycoproteins, lectins, nucleosides, nucleotides, nucleic acids, monosaccharides, disaccharides, trisaccharides, oligosaccharides, polysaccharides, lipopolysaccharides, vitamins, steroids, hormones, cofactors, receptors, receptor ligands, antibodies, antigen binding fragments of antibodies, and analogs and derivatives thereof.

50. The method of any of paragraphs 25-49, wherein the particle comprises both a targeting agent and at least one of a therapeutic agent, an imaging agent, a micronutrient, a tracking agent, or a chemotherapeutic agent.

51. The method of any of paragraphs 25-50, wherein the agent comprises about 0.01 wt % to about 99 wt % of the particle.

52. The method of any of paragraphs 25-51, wherein $10^5$ particles comprise from about 0.01 ng to about 100 ng of the agent.

53. The method of paragraph 25-52, wherein $10^5$ particles comprise from about 5 ng to about 15 ng of the agent.

54. The method of any of paragraphs 25-54, further comprising determining the effectiveness of a particle by performing a tissue regeneration assay.

55. The method of paragraph 54, wherein the tissue regeneration assay is a Platyhelminthes tissue regeneration assay.

56. A particle prepared by the method of any of paragraphs 25-55.

57. A pharmaceutical composition comprising a particle of any of paragraphs 1-24 or 56 and a pharmaceutically acceptable carrier.

58. A method comprising:
administering a particle or composition of any of paragraphs 1-24, 56, or 57 to a subject.

59. The method of paragraph 58, wherein the subject is in need of treatment for inflammation, wound healing, or pain management.

60. The method of any of paragraphs 58-59, wherein the inflammation is selected from the group consisting of:
skin inflammation; inflammation caused by substance abuse or drug addiction; inflammation associated with infection; inflammation of the cornea; inflammation of the retina; inflammation of the spinal cord; inflammation associated with organ regeneration; and pulmonary inflammation.

61. The method of any of paragraphs 58-60, wherein the subject is in need of treatment for a condition selected from the group consisting of:
temporomandibular joint disorders; COPD; smoke-induced lung injury; renal dialysis associated disorders; spinal cord injury; graft vs. host disease; bone marrow transplant or complications thereof; infection; trauma; pain; incisions; surgical incisions; a chronic pain disorder; a chronic bone disorder; mastitis; and joint disease.

62. The method of any of paragraphs 58-61, wherein said administration is injection, infusion, instillation, inhalation, ingestion, or topical.

63. The method of any of paragraphs 58-62, wherein the administration is local or systemic.

64. The method of any of paragraphs 58-63, wherein the particle is autologous to the subject.

65. The method of any of paragraphs 58-64, wherein the particle comprises a therapeutically effective amount of the agent.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This technology is further illustrated by the following examples which should not be construed as limiting.

EXAMPLES

Example 1: Humanized Nanoparticles Resolve Inflammation

Described herein are experiments in which endogenous microparticles (MPs) were systematically profiled during the time course of self-limited inflammation. Precursors for specialized pro-resolving lipid mediators (LM) were identified in MPs from inflammatory exudates utilizing LC-MS/MS-based metabolomics. Hence, it was postulated that formation of anti-inflammatory and pro-resolving LM could underlie beneficial effects attributed to MPs and that this process could serve as a basis for biomimicry. Using human neutrophil-derived MPs, novel nanoparticles (NPs) containing aspirin-triggered resolvin D1 (ATRvD1) or a lipoxin A4 (LXA4) analog were constructed. Enriched NPs dramatically reduced PMN influx in murine peritonitis, shortened resolution intervals and exhibited pro-resolving actions accelerating keratinocyte healing. The enriched NPs protected against inflammation in the temporomandibular joint (TMJ). These findings indicate that humanized NPs, termed nano-pro-resolving medicines (NPRMs) are mimetics of endogenous resolving mechanisms, possess potent beneficial bioactions, can reduce nanotoxicity and offer new therapeutic approaches.

Introduction

Uncontrolled inflammation is a fundamental aetiology of many pathologies, including cardiovascular diseases, arthritis and temporomandibular joint disorders (TMDs) (1, 2). Prevalence of TMDs is high, with at least one symptom afflicting a third of US adults. However, there is an unmet need for effective treatments as options are limited and often involve behavioral or physical therapies or acute administration of nonsteroidal anti-inflammatories (2). Timely resolution of an inflammatory insult is pertinent for restoration of tissue homeostasis and is essential for ongoing health (3). Thus endogenous control mechanisms of inflammation and its resolution are of considerable interest. Recently, potent specialized chemical mediators derived from essential fatty acids were identified that actively promote inflammation resolution via novel pro-resolving and anti-inflammatory cascades (4). Originally, microparticles (MPs) were thought to be inert empty vesicles. MPs are detected in physiological conditions, with increased numbers disseminated in multiple diseases including rheumatoid arthritis (5). Along these lines, anti-inflammatory properties of MPs shed from polymorphonuclear cells (PMNs) were uncovered (6, 7).

Herein, the temporal generation and properties of endogenous MPs produced in evolving self-limited inflammatory exudates in vivo were investigated and a novel biomimetic system was constructed, utilizing human PMN-derived MPs to stimulate resolution of inflammation as demonstrated in temporomandibular joint disease (TMJ). This biomimetic construction is highly advantageous as compared with other synthetic nanoparticle drug delivery systems that have adverse immunotoxic effects (8).

Materials and Methods

Endogenous Microparticles.

Peritonitis was initiated in male FVB mice (6-8 wk, Charles River) with zymosan A (1 mg i.p.) and peritoneal lavages were collected at indicated times. Exudate MPs were isolated by removal of leukocytes (4000 g, 15 min) followed by ultracentrifugation (100,000 g, 1 h) and quantified by flow cytometry. MPs were characterized with anti-CD1 1b (M1/70), CD54 (YN1), isotype control Abs (eBioscience) or CD45 (30-F11) (BD Biosciences) and annexinA5 (BD Biosciences) for external phosphatidylserine. For solid-phase extraction and LC-MS/MS based analyses cold methanol was added to MPs (9).

Preparation of Humanized Nano-Pro-Resolving Medicines (NPRMs).

Human MPs were prepared (6), and added to thin lipid films in glass flasks (after organic solvent removal by rotary evaporation; 10 min, 25° C.) containing fluorescent 1,2-dioleoyl-sn glycero-3-phoshpo-L-serine-N-7-nitro-2-1,3-benzoxadiazol-4-yl (100 µg, Avanti Polar Lipids) and 7S,8R,17R-trihydroxy-docosa-4Z,9E,11E,13Z,15E,19Z-hexaenoic acid (ATRvD1; 1 µg, Cayman Chemical) or o-[9,12]-benzo-ω6-epi-LXA$_4$ (1 µg) (10) prepared for these studies by contract custom synthesis. Intercalation of AT-RvD1 or LXA$_4$ analog and fluorescent phospholipid was performed by aqueous energy dissemination using a sonic dismembrator (output power 15W, 15 min, 25° C., Fisher Scientific). Humanized nanoparticles (NPs) were layered on Sephadex G50 columns (Sigma) and fractions collected in 0.2 µm-filtered PBS. Incorporation of AT-RvD1 and LXA$_4$ analog were determined using LC-MS/MS, and fluorescent phospholipid content confirmed by flow cytometry (BD FACSCanto II). NPs and MPs were sized using calibration beads (Corpuscular) by flow cytometry and conventional electron microscopy following negative staining (Tecnai™ G² Spirit BioTWIN; HMS core facility).

Mediator Lipidomics.

LC/UV/MS/MS-based mediator lipidomics analysis was performed with an HPLC (Shimadzu LC2OAD)-UV (Agilent 1100) coupled to a quadrupole ion-trap mass spectrometer (QTrap3200; Applied Biosystems) equipped with a C18 column (Agilent Eclipse Plus, 4.6 mm×50 mm×1.8 mm). Acquisition was conducted in negative ionization mode and LM were profiled using scheduled multiple reaction monitoring with identified using retention time, >5-6 diagnostic ions and matching criteria (9). Esterified monohydroxy-products were assessed in endogenous MPs following methanol/chloroform extraction of phospholipids and overnight saponification with 1N potassium hydroxide in 90% ethanol. Samples were acidified and extracted with added internal standard d$_5$-17-HDHA (1 ng) for LC-MS/MS based lipidomics as above.

For MP phosphatidylcholine analyses, LC-UV/MS/MS-based mediator lipidomic analysis was performed with an HPLC (Shimadzu LC2OAD) connected inline with a UV diode array detector (Agilent G1315B), coupled to a hybrid quadrupole time-of-flight mass spectrometer (QStar XL; Applied Biosystems) equipped with a Phenomenex Luna C18(2) column (2 mm×150 mm×31 µm). Mobile phase consisted of 0.5% ammonium hydroxide in methanol/acetonitrile/and 0.1M ammonium acetate (97:2:1; v/v/v) at 200 µl/min. Operating parameters and collision energies were optimized individually.

Peritonitis and Wound Healing.

Human MPs or NPRMs (1×10⁴-3×10⁵) were given i.v. (or i.p. as indicated) prior to zymosan A (0.1 mg i.p) and peritoneal leukocytes were assessed at 2, 4 or 12 h. In some experiments mice were given d$_5$-DHA (1 µg i.v.) prior to zymosan A (1 mg), and peritoneal MPs were collected at 4 h. Wound healing was assessed using an Electric Cell-substrate Impedance Sensing (ECIS) 1600R system (Applied Biophysics) (11). Human epidermal keratinocytes (Lonza) were cultured on 8W1E electrode arrays, and once confluent (~8,000Ω; using 16 kHz) were wounded (64 kHz, 30 s). Cells were treated with buffer alone, AT-RvD1 NPRMs (10 nM), AT-RvD1 (10 nM) or equivalent nanoparticle number.

Temporomandibular Joint (TMJ) Inflammation.

Mice were anesthetized (O$_2$:1 L/min, isoflurane 2.5%), and Complete Freund's adjuvant (CFA) was administered (10 µg; 20 µl) into the periarticular space of the left TMJ and 0.9% sterile saline (20 µl) into the right TMJ space as in (12). Treatments were then delivered i.v. with buffer (100 µA PBS), ATRvD1 (10 ng) NPRMs or o-[9,12]-benzo-ω6-epi-LXA$_4$ (10 ng) NPRMs. After 12 h PMN infiltration was assessed in the TMJ by myeloperoxidase (MPO) activity by ELISA (Hycult Biotechnology).

Statistics.

Data are mean±S.E.M. Multiple group comparisons were made using one-way ANOVA followed by Dunnett's or Bonferroni post hoc analysis. $p<0.05$ was considered significant.

Results and Discussion

Figure 1B:
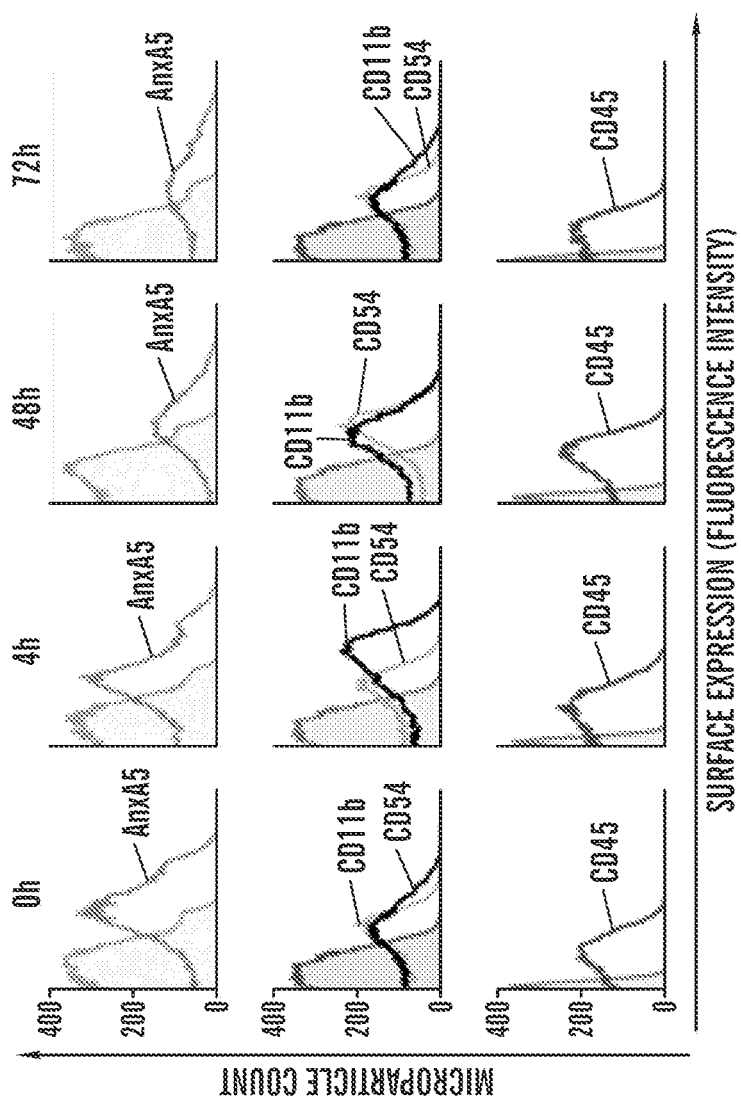
Figure 2A:
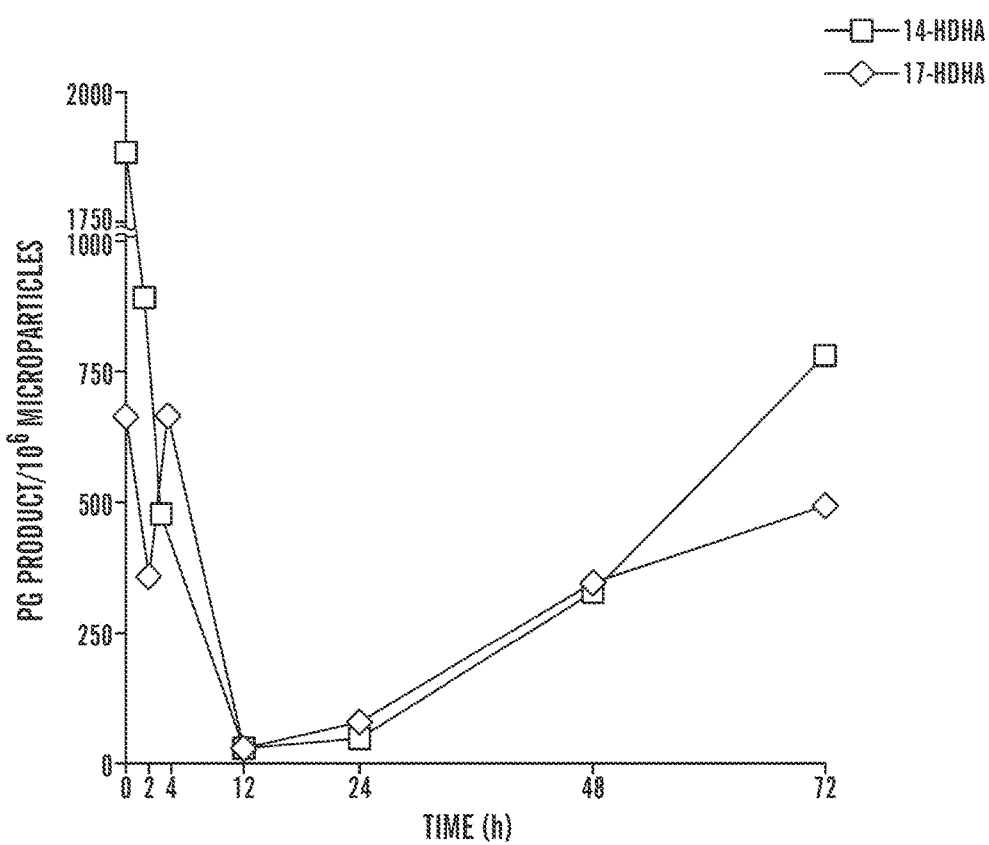
FIGS. 2A-2C demonstrate that endogenous leukocyte-derived microparticles contain resolvin precursors and LM pathway markers.
Figure 2B:
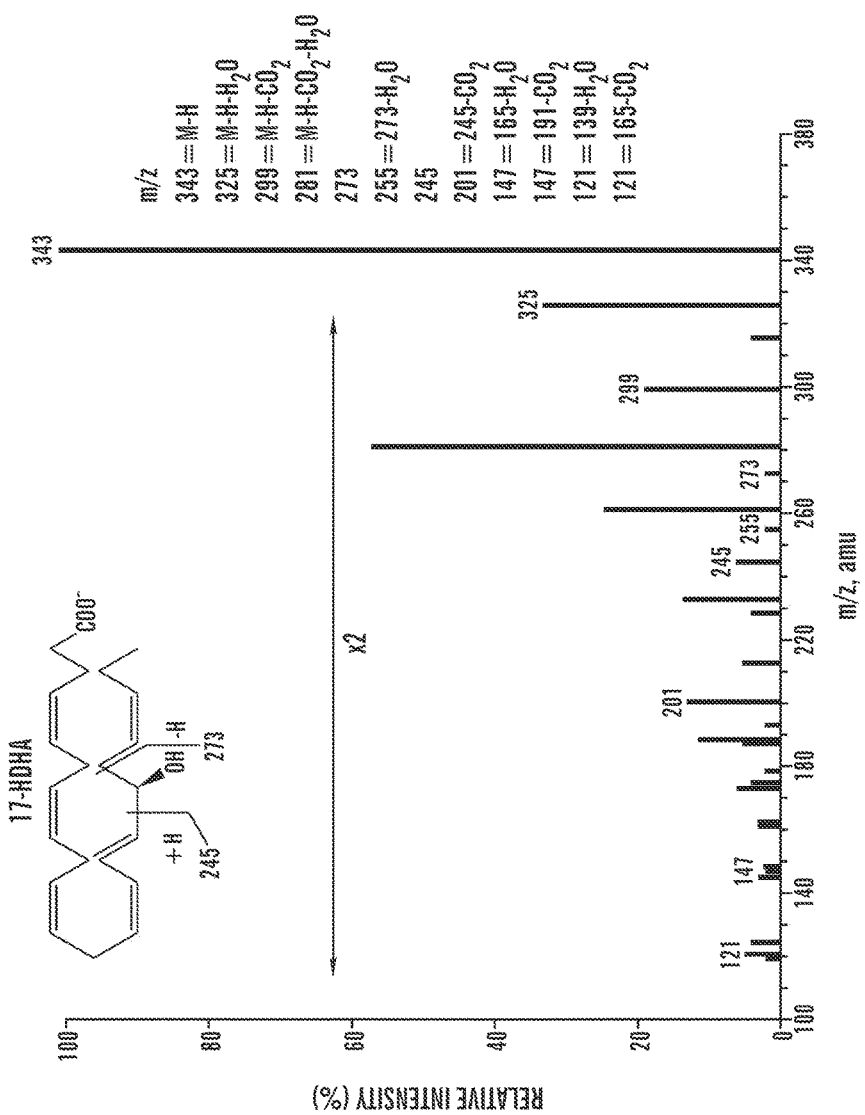

First, the time-course of MP generation in self-limited acute inflammation, i.e. zymosan-induced peritonitis, was profiled. The endogenous leukocyte-derived MPs were temporally generated in vivo in inflammatory exudates, with maximum MPs identified within the initiation phase, which gradually declined during the resolution phase corresponding with neutrophilic loss (FIG. 1A). Further characterization of these annexin $A5^+$ MPs by surface molecule expression demonstrated these were $CD11b^+$, $CD45^+$ and $CD54^+$ (FIG. 1B). To systematically address the lipid mediator (LM) profiles carried by endogenous MPs, liquid chromatography tandem mass spectrometry (LCMS/MS)-based metabolomics was performed. Endogenous MPs formed in inflammatory exudates were found to contain esterified biosynthetic precursors of novel specialized pro-resolving mediators (FIG. 2A). For example, the levels of MP-associated hydroxydocosahexaenoic acids; namely 14-HDHA and 17-HDHA were high during the initiation phase of acute inflammatory response, decreased during the peak of inflammation and accumulated in resolution, the phase in which potent anti-inflammatory and pro-resolving LM are biosynthesized (13). FIG. 2B shows a representative mass spectrum of 17-HDHA, with the diagnostic ions used for identification criteria denoted, including mass-to-charge ratio (m/z) 245 and 273. Notably, endogenous MPs were devoid of unesterified monohydroxy fatty acids, suggesting that once liberated from MP membranes, they are made available to leukocytes within the exudate.

Figure 2C:
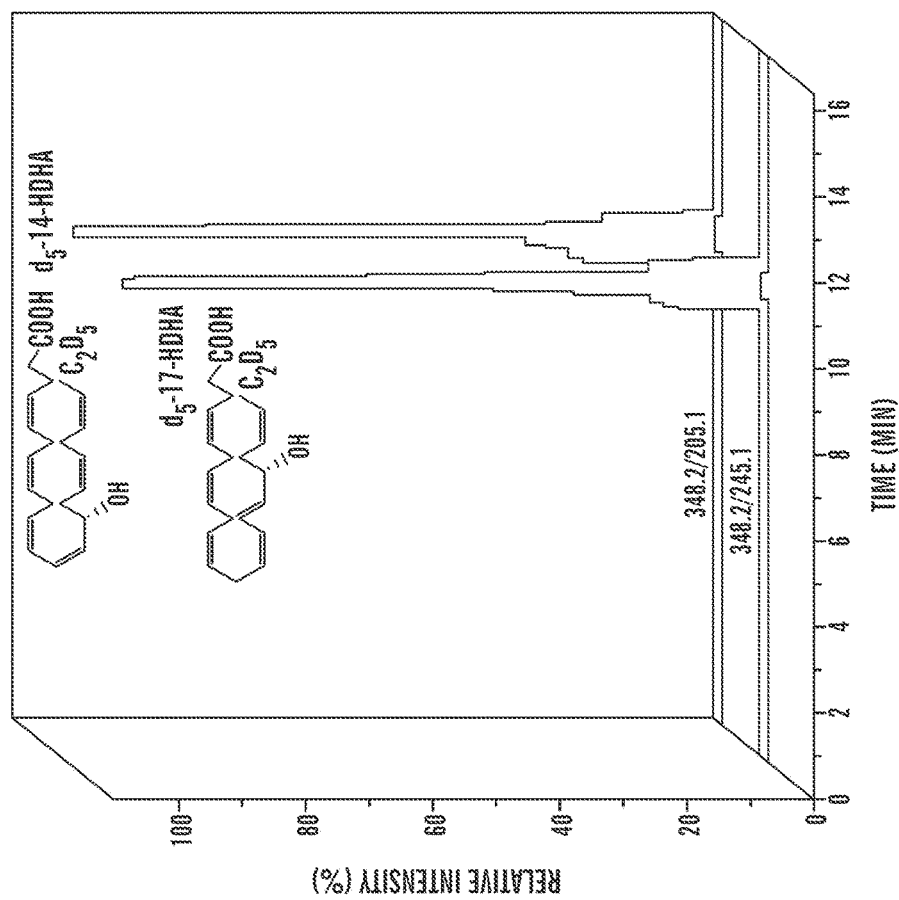
Figure 5B:
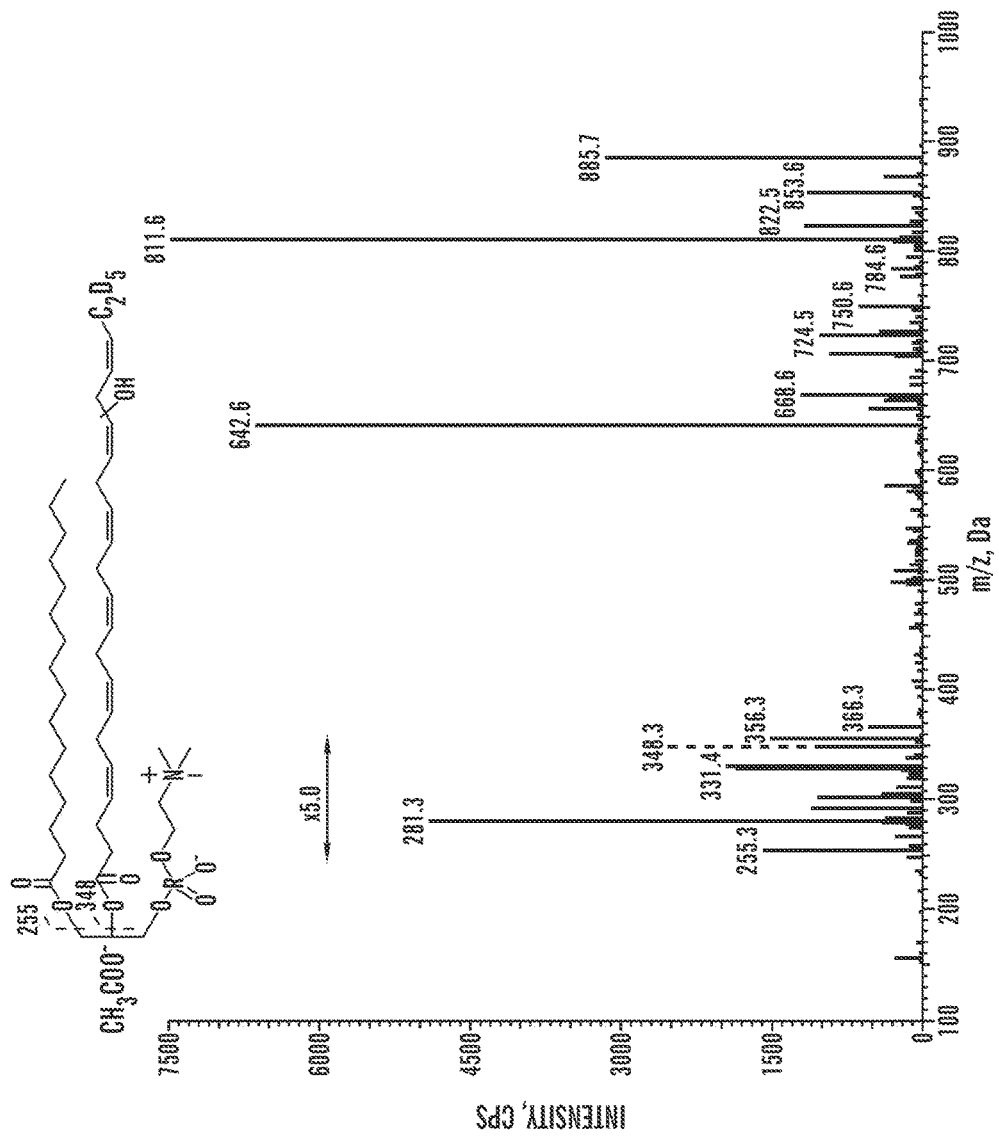

Following i.v administration of deuterium-labelled $d_5$-DHA for tracking, circulating $d_5$-DHA is made rapidly available to exudates (14) and was incorporated into endogenous MPs generated during the onset of acute inflammation. Additionally, these MPs also contained enzymatic metabolites of $d_5$-DHA, namely $d_5$-17-HDHA and $d_5$-14-HDHA, deuterated biosynthetic pathway biomarkers for D-series resolvins and maresin biosynthesis respectively, which reflects activation of these new pathways and their H(p)DHA intermediates (FIG. 2C). These results implicate endogenous MPs as intercellular communicators that can deliver pro-resolving LM precursors to inflammatory loci. Further experiments were performed to assess whether exogenous DHA was stored within MP phospholipids. When human PMN were incubated with $d_5$DHA, MPs were generated containing both $d_5$-DHA and $d_5$-HDHA esterified into phosphatidylcholine (FIGS. 5A-5B). Noteworthy, both cytosolic and secretory $PLA_2$ are induced during the resolution phase of inflammation (15). $sPLA_2$ added to resolving MP liberated esterified precursors from MPs (Table I).

Figure 6:
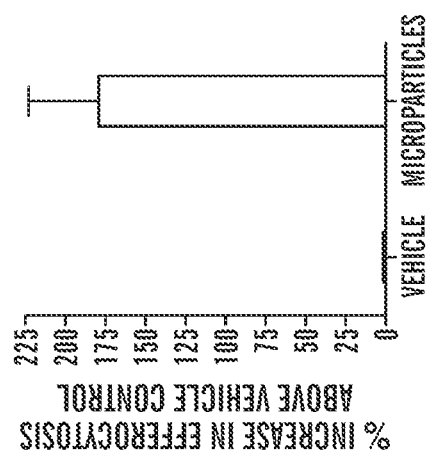
FIG. 6 demonstrates that microparticles enhance efferocytosis. Human monocyte derived macrophages (7-day differentiated with 10 ng/ml GM-CSF) were seeded at $1\times10^5$/well, and vehicle or MPs ($8\times10^5$) were added 15 min prior to addition of PKH26 (Sigma)-labeled human apoptotic PMN ($3\times10^5$). After 1 h macrophages were washed and efferocytosis was assessed using a PerkinElmer VICTOR™ plate reader.

Human PMN-derived MPs display anti-inflammatory properties via ALX/FPR2, the receptor for $LXA_4$, annexin-Al as well as Resolvin D1 (RvD1) (6, 16). Additionally, it is demonstrated herein that MPs enhanced efferocytosis (FIG. 6) and contain precursors for pro-resolving LM, thus likely contributing to the beneficial properties attributed to these MPs. Since many biomaterials used for nanoparticle drug delivery can activate the circulatory system and cause nanotoxicity, for example by uptake and activation of dendritic cells (8), new means to locally administer and activate pro-resolving cascades in vivo based on the endogenous MP system were sought. Thus, newly constructed nanomedicines should possess multi-pronged agonist actions in resolution, activating endogenous ALX, releasing precursors for local pro-resolving mediators as well as delivering their cargo of uploaded LM.

Figure 3A:
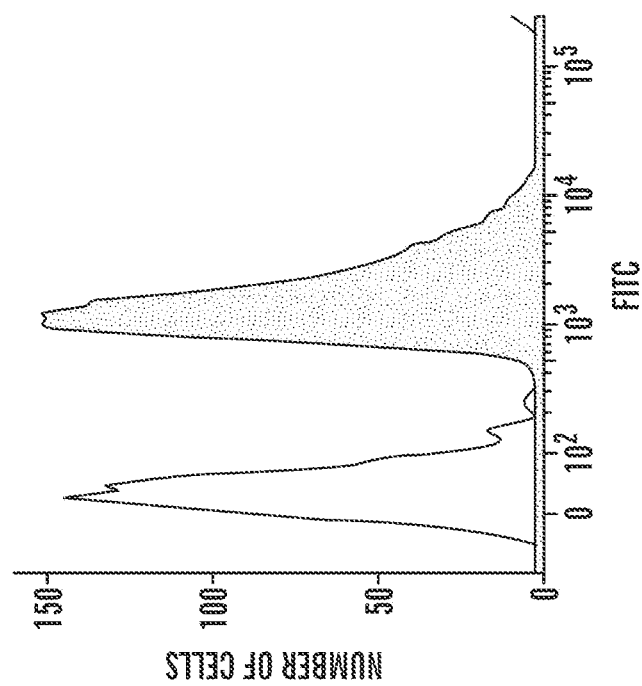
Figure 3B:
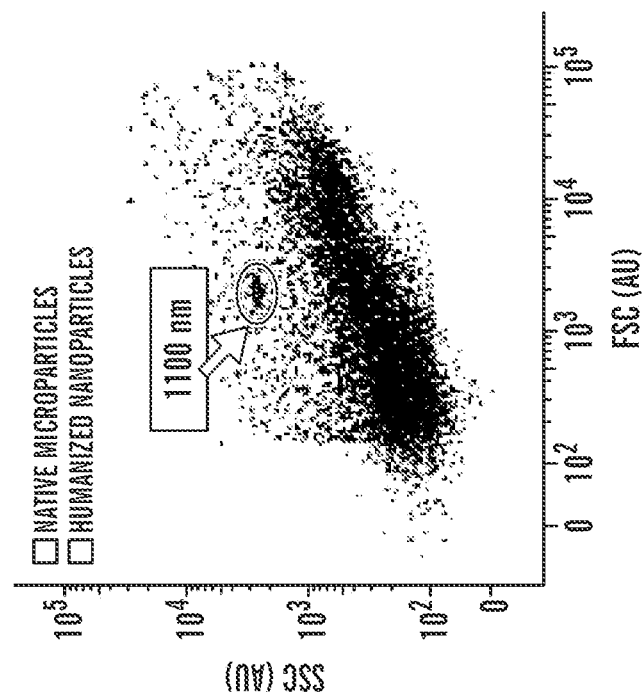
Figure 3F:
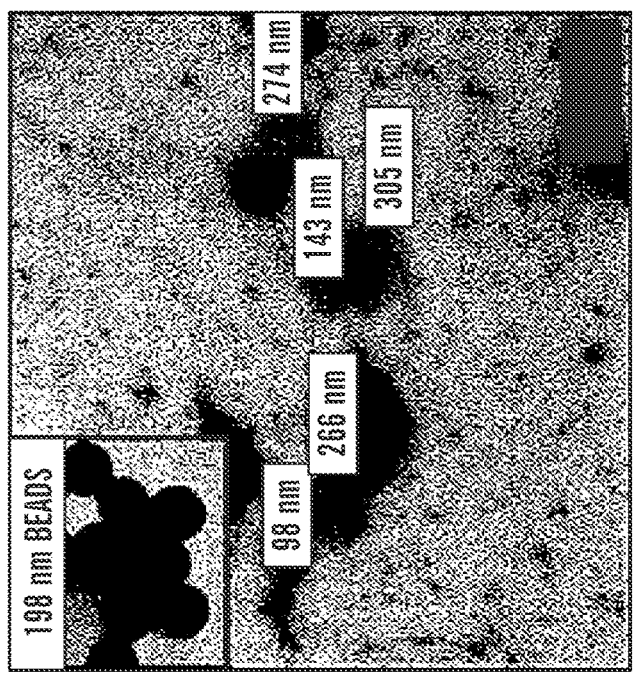
Figure 3E:
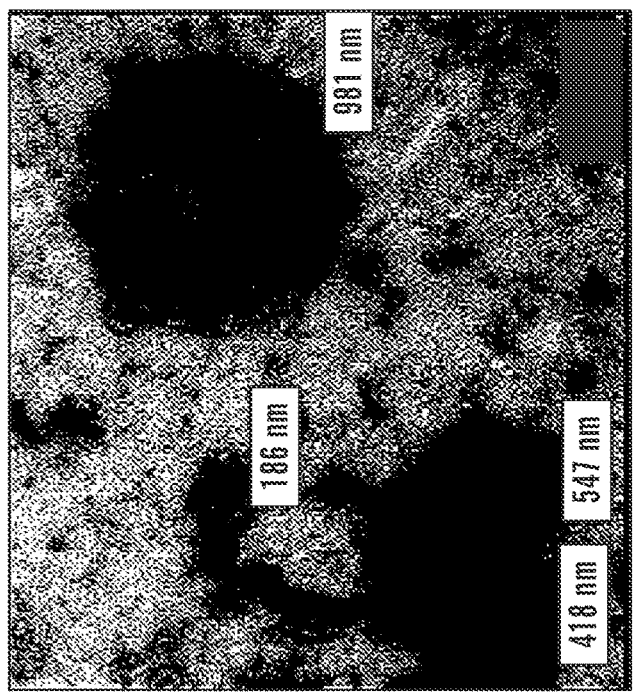
Figure 3G:
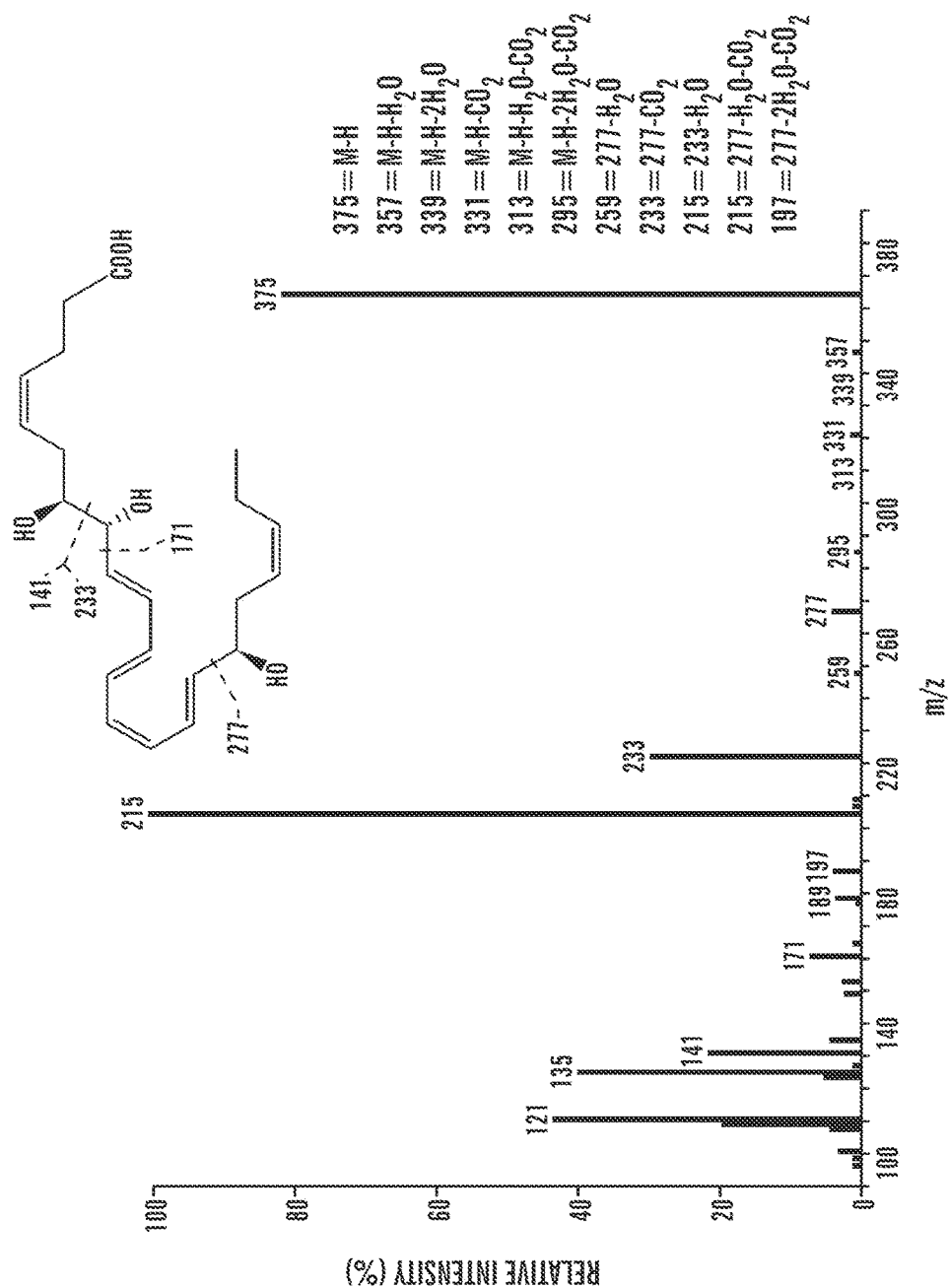

Harnessing human neutrophil-derived MPs as scaffolds, NPs containing either aspirin-triggered resolvin D1 (AT-RvD1) (4) or a stable analog of LXA4 (10) were constructed. Following enrichment procedures and energy induced conversion of MP to NPs, preparations were layered onto size-exclusion chromatography columns to separate free unincorporated lipids from MP-associated lipids, and eluate fractions were collected and taken for analyses including flow cytometry. Characteristically, enriched NPs (FIG. 3A) were smaller than their MP counterparts (FIG. 3A) and also contained fluorescent phospholipid (FIG. 3B, right peak). Nanoparticle sizing was accomplished by flow cytometry using nanosphere calibration beads (FIGS. 3C-3D) Sizing was further validated using negative stain electron microscopy of MPs (FIG. 3E) and NPRMs (FIG. 3F). Both methods showed smaller, more uniform sizing of NPs following enrichment procedures. Prior to each experiment, incorporation of AT-RvD1 or the LXA4 analog was determined using LC-MS/MS. Representative tandem mass spectrum of nanoparticle associated AT-RvD1 (m/z 375.2) is shown from scheduled multiple reaction monitoring (MRM) of the m/z 375.2/215 transition pair at 7.4 min (FIG. 3G).

Figure 4B:
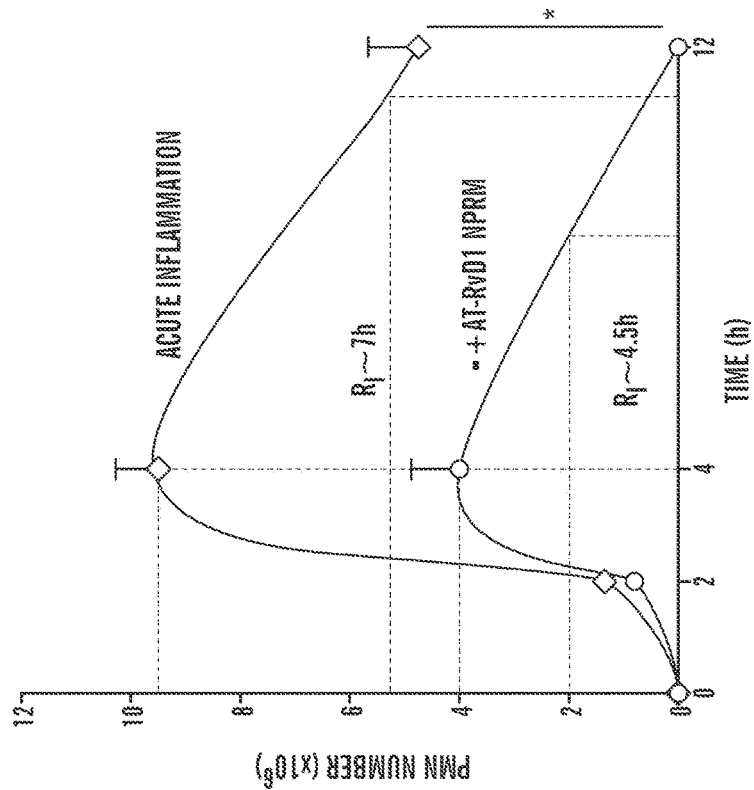
FIGS. 4A-4D demonstrate that nano-pro-resolving medicines limit PMN infiltration to inflammatory sites, enhance wound healing and are protective in TMJ.
Figure 4A:
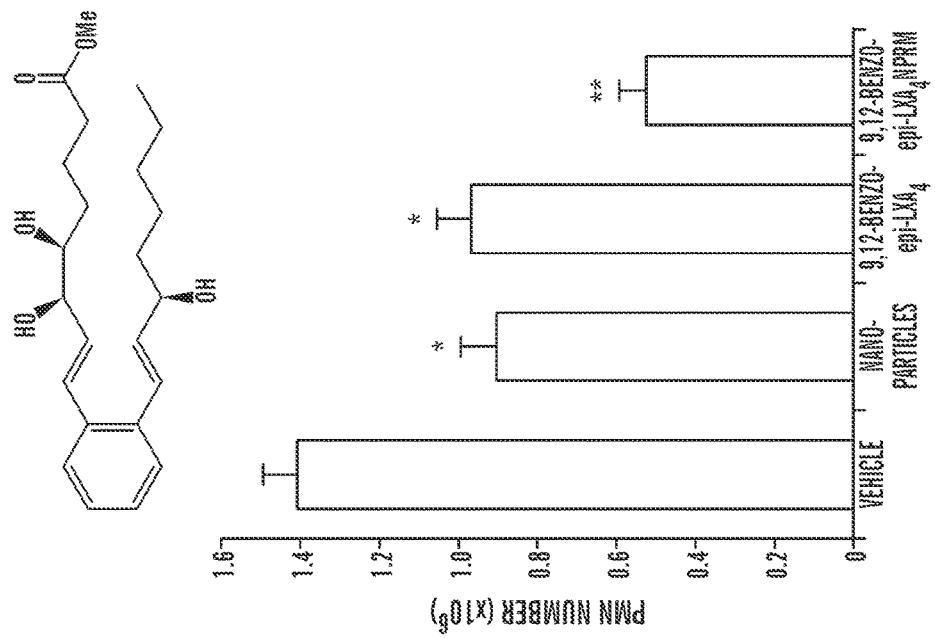
Figure 7A:
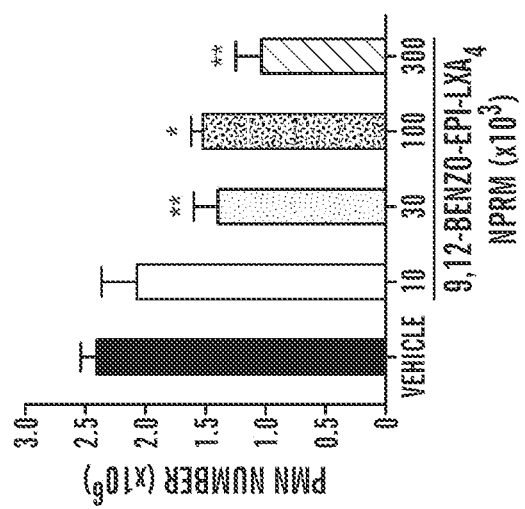
FIGS. 7A-7B demonstrate that nano-pro-resolving medicines reduce peritoneal PMN infiltration. Human NPRMs ($1\times10^4$-$3\times10^5$) were given (FIG. 7A) i.v.
Figure 7B:
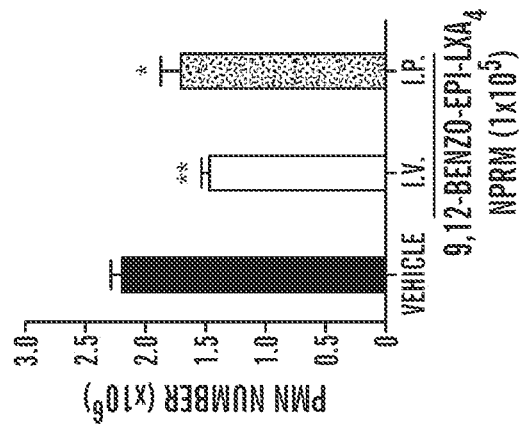

These humanized NPs were inherently anti-inflammatory, even without enriching with LM, counter-regulating PMN infiltration in acute zymosan (0.1 mg) peritonitis by ~25% following i.v. administration of $1\times10^5$ NPs (FIG. 4A). A similar reduction in PMN influx was observed with 300 ng of a stable $LXA_4$ analog consistent with earlier findings (17). Remarkably, when the LXA4 analog was incorporated into human NPs, they drastically limited PMN numbers by ~60% showing they possess additional anti-inflammatory properties. Importantly, $1\times10^5$ NPs equated to an incorporation of 5.0-8.8 ng of LX analog, effectively demonstrating that much lower amounts were needed locally to reduce PMN infiltration than analog alone. This proved dose dependent, with maximal NPRMs greatly limiting PMN recruitment (FIGS. 7A-7B). An inhibitory action on PMN recruitment when NPRMs were administered directly into the peritoneum was found, suggesting a direct action on resident macrophages, dampening their inflammatory response to zymosan (FIG. 7B). Bioactivity of AT-RvD1 enriched NPs was assessed in murine peritonitis. Leukocyte recruitment and differential analyses were assessed at 3 separate intervals in order to quantify acute inflammatory response using self-limited inflammation (FIG. 4B). Local microbial administration resulted in a rapid increase in PMN infiltration, which peaked at 4 h post-challenge corresponding to the onset of inflammation. By 12 h PMNs had declined, and the resolution interval ($R_i$) was calculated (i.e. time taken for maximal PMN to decrease 50%). NPs carrying AT-RvD1 drastically reduced PMN recruitment in microbial peritonitis, reducing maximal PMN infiltration from $9.4\pm0.7\times10^6$ to $4.0\pm0.8\times10^6$ and also shortened R, from 7 h to ~4.5 h (FIG. 4B).

Figures 4C, 4D:
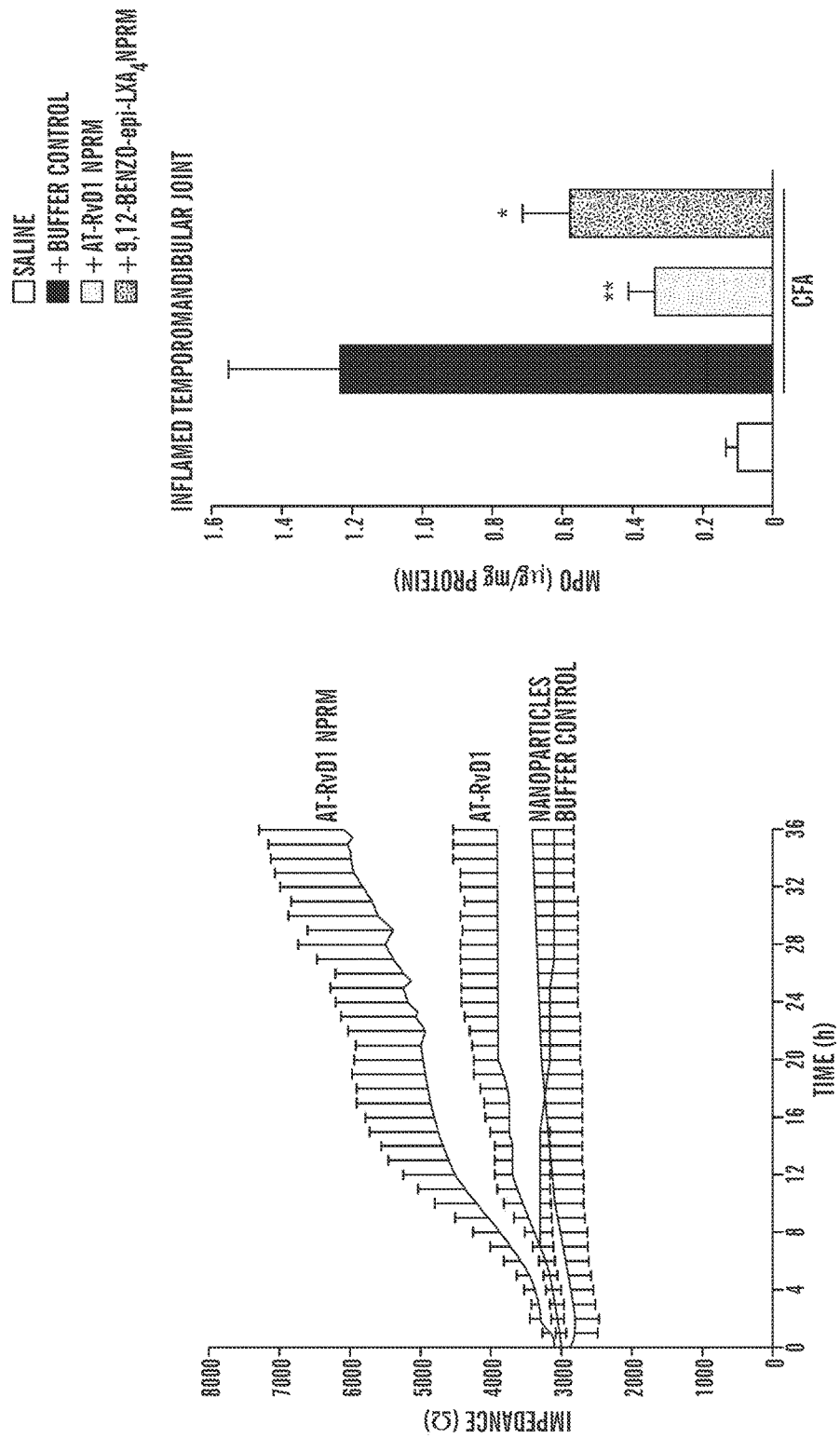

Pro-resolving bioactions of these humanized nanomedicines were next evaluated in a keratinocyte wound-healing assay using in vitro epidermal abrasion (11). Following focal clearance of keratinocytes with an elevated electrical field pulse, keratinocyte healing from the perimeter into the clearance zone was assessed in real-time by impedance sensing. This highly sensitive method indicated that AT-RvD1 containing nanomedicines enhanced wound closure rates as compared with either non-enriched NPs or with equimolar amounts of AT-RvD1 (10 nM), demonstrating their pro-resolving properties (FIG. 4C).

Temporomandibular joint disorders are a significant clinical problem, causing craniofacial pain (2). Effective treatment of pain arising from inflammation of joints and muscles remains an unmet medical need, and is implicated not only in TMDs but also in many other human diseases. To this end, whether these nanomedicines would confer protection against CFA-induced inflammation of the TMJ was evaluated. Indeed, 10 ng of either AT-RvD1 NPRMs or o-[9,12]-benzo-ω6-epi-LXA$_4$ NPRMs drastically reduced the number of infiltrating PMN into the inflamed TMJ 12 h after CFA-induced inflammation (FIG. 4D). Importantly, MPO levels in the contralateral TMJ were not elevated, and no significant differences were noted between buffer control and NPRM treatment groups (not shown). Of relevance, both RvD1 and RvE1 also attenuate inflammatory pain (18). Together these results establish that biomimicking endogenous resolution mechanisms centred on anti-inflammatory and pro-resolving MPs, enhances the bioactions of potent LM. Nanoparticle delivery of AT-RvD1 or a stable analog of LXA$_4$ prevented excessive neutrophilic infiltration to inflamed TMJs thus circumventing ensuing granuloma formation and further joint destruction associated with overzealous leukocyte recruitment in this complex joint disease.

REFERENCES

1. Nathan, C., and A. Ding. 2010. Nonresolving inflammation. *Cell* 140:871-882.
2. Scrivani, S. J., D. A. Keith, and L. B. Kaban. 2008. Temporomandibular disorders. *N Engl J Med* 359:2693-2705.
3. Gilroy, D. W., T. Lawrence, M. Perretti, and A. G. Rossi. 2004. Inflammatory resolution: new opportunities for drug discovery. *Nat Rev Drug Discov* 3:401416.
4. Serhan, C. N. 2007. Resolution phase of inflammation: novel endogenous anti-inflammatory and proresolving lipid mediators and pathways. *Annu Rev Immunol* 25:101-137.
5. Boilard, E., P. A. Nigrovic, K. Larabee, G. F. Watts, J. S. Coblyn, M. E. Weinblatt, E. M. Massarotti, E. Remold-O'Donnell, R. W. Farndale, J. Ware, and D. M. Lee. 2010. Platelets amplify inflammation in arthritis via collagen-dependent microparticle production. *Science* 327:580-583.
6. Dalli, J., L. V. Norling, D. Renshaw, D. Cooper, K. Y. Leung, and M. Perretti. 2008. Annexin 1 mediates the rapid anti-inflammatory effects of neutrophilderived microparticles. *Blood* 112:2512-2519.
7. Gasser, O., and J. A. Schifferli. 2004. Activated polymorphonuclear neutrophils disseminate anti-inflammatory microparticles by ectocytosis. *Blood* 104:2543-2548.
8. Hess, H., and Y. Tseng. 2007. Active intracellular transport of nanoparticles: opportunity or threat? *ACS Nano* 1:390-392.
9. Serhan, C. N., Y. Lu, S. Hong, and R. Yang. 2007. Mediator lipidomics: search algorithms for eicosanoids, resolvins, and protectins. *Methods Enzymol* 432:275-317.
10. Petasis, N. A., R. Keledjian, Y. P. Sun, K. C. Nagulapalli, E. Tjonahen, R. Yang, and C. N. Serhan. 2008. Design and synthesis of benzo-lipoxin A4 analogs with enhanced stability and potent anti-inflammatory properties. *Bioorg Med Chem Lett* 18:1382-1387.
11. Keese, C. R., J. Wegener, S. R. Walker, and I. Giaever. 2004. Electrical wound-healing assay for cells in vitro. *Proc Natl Acad Sci USA* 101:1554-1559.
12. Kramer, P. R., C. A. Kerins, E. Schneiderman, and L. L. Bellinger. 2010. Measuring persistent temporomandibular joint nociception in rats and two mice strains. *Physiol Behav* 99:669-678.
13. Serhan, C. N., R. Yang, K. Martinod, K. Kasuga, P. S. Pillai, T. F. Porter, S. F. Oh, and M. Spite. 2009. Maresins: novel macrophage mediators with potent antiinflammatory and proresolving actions. *J Exp Med* 206:15-23.
14. Kasuga, K., R. Yang, T. F. Porter, N. Agrawal, N. A. Petasis, D. Irimia, M. Toner, and C. N. Serhan. 2008. Rapid appearance of resolvin precursors in inflammatory exudates: novel mechanisms in resolution. *J Immunol* 181:8677-8687.
15. Gilroy, D. W., J. Newson, P. Sawmynaden, D. A. Willoughby, and J. D. Croxtall. 2004. A novel role for phospholipase A2 isoforms in the checkpoint control of acute inflammation. *FASEB J* 18:489-498.
16. Krishnamoorthy, S., A. Recchiuti, N. Chiang, S. Yacoubian, C. H. Lee, R. Yang, N. A. Petasis, and C. N. Serhan. 2010. Resolvin D1 binds human phagocytes with evidence for proresolving receptors. *Proc Natl Acad Sci USA* 107:1660-1665.
17. Sun, Y. P., E. Tjonahen, R. Keledjian, M. Zhu, R. Yang, A. Recchiuti, P. S. Pillai, N. A. Petasis, and C. N. Serhan. 2009. Anti-inflammatory and pro-resolving properties of benzo-lipoxin A(4) analogs. *Prostaglandins Leukot Essent Fatty Acids* 81:357-366.
18. Xu, Z. Z., L. Zhang, T. Liu, J. Y. Park, T. Berta, R. Yang, C. N. Serhan, and R. R. Ji. 2010. Resolvins RvE1 and RvD1 attenuate inflammatory pain via central and peripheral actions. *Nat Med* 16:592-597, 591p following 597.

TABLE 1

Microparticle fatty acid liberation with sPLA$_2$. Microparticles were collected from zymoan peritonitis (1 mg, i.p.) exudates at 48 h and incubated with or without human recombinant secretory PLA2 type V (0.7U, Cayman Chemical) for 30 min at 37° C., and liberation of fatty acids was assessed using LCMS/MS.

|  | DHA (pg) | EPA (pg) | AA (pg) | 17-HDHA (pg)* | 14-HDHA (pg)* | 5-HETE (pg)* | 12-HETE (pg)* | 15-HETE (pg)* |
|---|---|---|---|---|---|---|---|---|
| MP | 568 | 205 | 855 | 0.56 | 2.22 | 1.62 | 3.58 | 2.22 |
| MP + sPLA$_2$ | 5750 | 1620 | 10400 | 5.8 | 9.55 | 15.3 | 34.6 | 9.18 |

*Monohydroxy fatty acids were identified by retention time and multiple reaction monitoring. Transition pairs: 17-HDHA 343, 245; 14-HDHA 343, 205; 5-HETE 319, 115; 12-HETE 319, 179 and 15-HETE 319, 219.

Example 2: Particle Construction

In some embodiments, the particles described herein can be constructed as follows: Microparticles are generated from isolated human neutrophils following stimulation of the neutrophils. Purity of the microparticles can be assessed by Annexin V and CD66 staining. Organic solvents can be evaporated from compounds of interest to be used for tracking and/or treatment. The human microparticles can be added to the compounds of interest and the mixture agitated for 15 minutes.

The microparticle suspension can then be sonicated for 15 minutes at 15 W of output power to obtain compound intercalation to the microparticles. The resulting particles can be run over Sephadex G50 columns (Sigma) and fractions collected in 0.2 µm-filtered DPBS for subsequent analysis. Incorporation of a compound of interest can be established using appropriate methodology. For example, lipid mediators can be assessed by ELISA where available or LC-MS/MS-based methods. Similarly, incorporation of a tracking agent can be assessed using appropriate methodology. The size of the particles can be characterized using calibration beads of flow-cytometry and/or conventional electron microscopy.

What is claimed herein is:

1. An in vitro anti-inflammatory particle comprising:
   at least one component of a humanized cellular-derived microparticle selected from the group consisting of: Resolvin D1, Resolvin D2, Resolvin D3, Resolvin D5, Resolvin D6, Maresin 1, and Protectin D 1;
   and at least one anti-inflammatory therapeutic agent;
   wherein the at least one component of a humanized cellular-derived microparticle has a pro-resolving anti-inflammatory property.

2. The anti-inflammatory particle of claim 1, wherein the humanized cellular-derived microparticle is generated in vitro by contacting a cell with a leukocyte agonist.

3. The anti-inflammatory particle of claim 2, wherein the leukocyte agonist is selected from the group consisting of: IL-8; fMLP; IL-4; zymosan; LPS; leukotriene B4; and C5a.

4. The anti-inflammatory particle of claim 1, wherein the agent comprises about 0.01 wt % to about 99 wt % of the particle.

5. The anti-inflammatory particle of claim 1, wherein the particle comprises from about 0.1 fg to about 1000 fg of the agent.

6. The anti-inflammatory particle of claim 1, wherein the particle comprises from about 50 fg to about 150 fg of the agent.

7. The anti-inflammatory particle of claim 1, wherein the particle is of a size from about 100 nm to about 1.5 µm in diameter.

8. The anti-inflammatory particle of claim 1, wherein the at least one component of the cellular-derived microparticle comprises analogs and mimetics thereof.

9. The anti-inflammatory particle of claim 1, wherein the anti-inflammatory property of the anti-inflammatory particle is capable of decreasing at least one of a sign, a condition, and/or a symptom of inflammation.

10. The anti-inflammatory particle of claim 9, wherein the at least one of a sign, a condition, and/or a symptom of inflammation comprises an inflammatory condition of a skin, an inflammatory condition of a lung, an inflammatory condition of a joint, an inflammatory condition of a gut, an inflammatory condition of an eye, an inflammatory condition of a endocrine system, an inflammatory condition of a cardiovascular system, an inflammatory condition of a kidney, an inflammatory condition of a liver, an inflammatory condition of a central nervous system, and/or a sepsis-associated condition.

* * * * *